United States Patent
Galvin et al.

(10) Patent No.: US 8,222,413 B2
(45) Date of Patent: Jul. 17, 2012

(54) METHODS FOR SYNTHESIZING HETEROCYCLIC COMPOUNDS

(75) Inventors: Gabriel Galvin, Emeryville, CA (US); Eric Harwood, Emeryville, CA (US); David Ryckman, Emeryville, CA (US); Shuguang Zhu, Emeryville, CA (US)

(73) Assignee: Novartis AG, Emeryville, CA (US)

( * ) Notice: Subject to any disclaimer, the term of this patent is extended or adjusted under 35 U.S.C. 154(b) by 580 days.

(21) Appl. No.: 11/920,078

(22) PCT Filed: May 17, 2006

(86) PCT No.: PCT/US2006/019349
§ 371 (c)(1), (2), (4) Date: Jul. 21, 2009

(87) PCT Pub. No.: WO2006/125130
PCT Pub. Date: Nov. 23, 2006

(65) Prior Publication Data
US 2011/0046376 A1    Feb. 24, 2011

Related U.S. Application Data

(60) Provisional application No. 60/681,893, filed on May 17, 2005.

(51) Int. Cl.
C07D 401/00 (2006.01)
C07D 403/00 (2006.01)
(52) U.S. Cl. ...................... 544/362; 544/370
(58) Field of Classification Search .......... 544/362, 544/370
See application file for complete search history.

(56) References Cited

U.S. PATENT DOCUMENTS

| | | | |
|---|---|---|---|
| 3,663,606 A | 5/1972 | Isowa | |
| 4,659,657 A | 4/1987 | Harnisch et al. | |
| 5,330,992 A | 7/1994 | Eissenstat et al. | |
| 5,414,088 A | 5/1995 | Von Der Saal et al. | |
| 5,585,380 A | 12/1996 | Bianco et al. | |
| 5,646,153 A | 7/1997 | Spada et al. | |
| 5,710,158 A | 1/1998 | Myers et al. | |
| 5,763,441 A | 6/1998 | App et al. | |
| 5,792,771 A | 8/1998 | App et al. | |
| 5,801,212 A | 9/1998 | Okamoto et al. | |
| RE36,256 E | 7/1999 | Spada et al. | |
| 5,981,569 A | 11/1999 | App et al. | |
| 6,057,320 A | 5/2000 | Spada et al. | |
| 6,137,010 A | 10/2000 | Joo et al. | |
| 6,174,912 B1 | 1/2001 | Beck et al. | |
| 6,258,951 B1 | 7/2001 | Lohmann et al. | |
| 6,303,600 B1 | 10/2001 | Cox et al. | |
| 6,306,874 B1 | 10/2001 | Fraley et al. | |
| 6,313,138 B1 | 11/2001 | Fraley et al. | |
| RE37,650 E | 4/2002 | Myers et al. | |
| 6,420,382 B2 | 7/2002 | Fraley et al. | |
| 6,479,512 B1 | 11/2002 | Fraley et al. | |
| 6,593,344 B1 | 7/2003 | Biedermann et al. | |
| 6,605,617 B2 | 8/2003 | Renhowe et al. | |
| 6,756,383 B2 | 6/2004 | Renhowe et al. | |
| 6,759,417 B2 | 7/2004 | Renhowe et al. | |
| 6,762,194 B2 | 7/2004 | Renhowe et al. | |
| 6,774,237 B2 | 8/2004 | Renhowe et al. | |
| 6,800,760 B2 | 10/2004 | Renhowe et al. | |
| 7,064,215 B2 | 6/2006 | Renhowe et al. | |
| 7,179,912 B2 | 2/2007 | Halbrook et al. | |
| 2002/0103230 A1 | 8/2002 | Renhowe et al. | |
| 2002/0107392 A1 | 8/2002 | Renhowe et al. | |
| 2002/0165218 A1* | 11/2002 | Halbrook et al. | .......... 514/210.2 |
| 2003/0028018 A1 | 2/2003 | Renhowe et al. | |
| 2003/0158224 A1 | 8/2003 | Renhowe et al. | |
| 2003/0207883 A1 | 11/2003 | Renhowe et al. | |
| 2004/0092535 A1 | 5/2004 | Barsanti et al. | |

(Continued)

FOREIGN PATENT DOCUMENTS

DE        2363459        6/1975

(Continued)

OTHER PUBLICATIONS

Antonios-McCrea, W. R. et al., "LHMDS mediated tandem acylation-cyclization of 2-aminobenzenecarbonitriles with 2-benzymidazol-2-yl acetates: a short and efficient route to the synthesis of 4-amino-3-benzimidazol-2-ylhydroquinolin-2-ones," *Tetrahedron Letters*, vol. 47, 2006, pp. 657-660; published by Elsevier Ltd.

Bastin, et al., "Salt Selection and Optimisation Procedures for Pharmaceutical New Chemical Entities," *Organic Process Research & Development*, vol. 4, pp. 427-435, 2000.

Beck, J. R., "A Direct Synthesis of Benzo[b]thiophene-2-carboxylate Esters Involving Nitro Displacement," *J. Org. Chem.*, vol. 37, No. 21, 1972, pp. 3224-3226.

(Continued)

*Primary Examiner* — Andrew D Kosar
*Assistant Examiner* — Erich A Leeser
(74) *Attorney, Agent, or Firm* — Cozette M McAvoy

(57) ABSTRACT

A method for synthesizing a heterocyclic compound includes: reacting 1-methylpiperazine with 5-chloro-2-nitroaniline at an internal temperature sufficient to provide a compound of Formula VIH The 1-methylpiperazine and the 5-chloro-2-nitroaniline are reacted in a solvent that comprises water in an amount greater than 50 percent by volume based on the amount of the solvent and/or are reacted in a solvent that comprises an organic solvent component that has a boiling point of greater than 100° C. at atmospheric pressure.

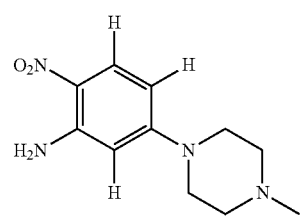

23 Claims, No Drawings

U.S. PATENT DOCUMENTS

| | | | |
|---|---|---|---|
| 2004/0220196 A1 | 11/2004 | Hannah et al. | |
| 2005/0137399 A1* | 6/2005 | Cai et al. | 544/363 |
| 2005/0203101 A1 | 9/2005 | Barsanti et al. | |
| 2005/0209247 A1* | 9/2005 | Cai et al. | 514/253.07 |
| 2005/0239825 A1 | 10/2005 | Lee et al. | |
| 2005/0256157 A1 | 11/2005 | Gesner et al. | |
| 2005/0261307 A1 | 11/2005 | Cai et al. | |

FOREIGN PATENT DOCUMENTS

| | | |
|---|---|---|
| DE | 3634066 | 4/1988 |
| DE | 19841985 | 3/2000 |
| EP | 0 290 153 | 11/1988 |
| EP | 0 508 800 | 10/1992 |
| EP | 0 509 717 | 10/1992 |
| EP | 0 747 771 | 12/1996 |
| EP | 0 797 376 | 9/1997 |
| HU | P0104752 | 7/2002 |
| JP | 59-130284 | 7/1984 |
| JP | 63230687 | 9/1988 |
| JP | 63-258903 | 10/1988 |
| JP | 6-9952 | 1/1994 |
| JP | 7-43896 | 2/1995 |
| JP | 8-29973 | 2/1996 |
| WO | WO 92/18483 | 10/1992 |
| WO | WO 92/20642 | 11/1992 |
| WO | WO 95/15758 | 6/1995 |
| WO | WO 95/18801 | 7/1995 |
| WO | WO 97/03069 | 1/1997 |
| WO | WO 97/34876 | 9/1997 |
| WO | WO 97/48694 | 12/1997 |
| WO | WO 98/13350 | 4/1998 |
| WO | WO 99/10349 | 3/1999 |
| WO | WO 99/50263 | 10/1999 |
| WO | WO 99/65897 | 12/1999 |
| WO | WO 00/00481 | 1/2000 |
| WO | WO 00/03990 | 1/2000 |
| WO | WO 00/20400 | 4/2000 |
| WO | WO 00/27379 | 5/2000 |
| WO | WO 00/58315 | 10/2000 |
| WO | WO 00/71129 | 11/2000 |
| WO | WO 01/02369 | 1/2001 |
| WO | WO 01/12169 | 2/2001 |
| WO | WO 01/28993 | 4/2001 |
| WO | WO 01/29025 | 4/2001 |
| WO | WO 01/52875 | 7/2001 |
| WO | WO 01/52904 | 7/2001 |
| WO | WO 01/53268 | 7/2001 |
| WO | WO 01/55114 | 8/2001 |
| WO | WO 01/62251 | 8/2001 |
| WO | WO 01/62252 | 8/2001 |
| WO | WO 02/18383 | 3/2002 |
| WO | WO 02/22598 | 3/2002 |
| WO | WO 02/26716 | 4/2002 |
| WO | WO 02/32861 | 4/2002 |
| WO | WO 02/058697 | 8/2002 |
| WO | WO 03/004488 | 1/2003 |
| WO | WO 03/033472 | 4/2003 |
| WO | WO 03/087095 | 10/2003 |
| WO | WO 2004/018419 | 3/2004 |
| WO | WO 2004/030620 | 4/2004 |
| WO | WO 2004/031401 | 4/2004 |
| WO | WO 2004/043389 | 5/2004 |
| WO | WO 2004/063151 | 7/2004 |
| WO | WO 2004/063170 * | 7/2004 |
| WO | WO 2004/087153 | 10/2004 |
| WO | WO 2005/046589 | 5/2005 |
| WO | WO 2005/046590 | 5/2005 |
| WO | WO 2005/053692 | 6/2005 |
| WO | WO 2005/082340 | 9/2005 |
| WO | WO 2006/081445 | 8/2006 |

OTHER PUBLICATIONS

Carling, R. W. et al., "4-Substituted-3-phenylquinolin-2(1*H*)-ones: Acidic and Nonacidic Glycine Site *N*-Methyl-D-aspartate Antagonists with in Vivo Activity," *J. Med. Chem.*, vol. 40, 1997, pp. 754-765; published by American Chemical Society.
CAS printout for 300591-52-0 Registry File, entry date into Registry File Oct. 31, 2000.
CAS printout for 304876-79-7 Registry File, entry date into Registry File Nov. 29, 2000.
Cecil, Textbook of Medicine, 21$^{st}$ Edition (2000), Goldman & Bennett (Editors), W.B. Saunders Company (Publisher), Chapter 198, pp. 1060-1074).
Charvat, T. et al., "Diethyl Acetonedicarboxylate—a Precursor for the Synthesis of New Substituted 4-Aminoquinolines and Fused 4-Aminopyridines," *Monatshefte für Chemie*, vol. 126, 1995, pp. 333-340.
Gewald, K. et al., "4-Amino-3-pyridiniochinolin-2(1*H*)-on-chloride und 3,4-Diaminochinolin-2(1*H*)-one," *Chem. Ber.*, vol. 124, 1991, pp. 1237-1241, Eng. Abstract provided; published by VCH Verlagsgesellschaft mbH.
Hennequin, L. F., et al., Design and Structure—Activity Relationship of a New Class of Potent VEGF Receptor Tyrosine Kinase Inhibitors,: *J. Med. Chem.*, vol. 42, No. 26, pp. 5369-5389, 1999; published by American Chemical Society, Washington, D.C.
Hiyama, T. et al., "A New Synthesis of 3-Amino-2-Alkenoates," *Tetrahedron Letters*, vol. 23, No. 15, 1982, pp. 1597-1600; published by Pergamon Press Ltd.
International Search Report for PCT/US04/37051 dated Aug. 31, 2005.
International Search Report for PCT/US06/19349 dated Sep. 11, 2006.
Lee, S. H. et al., "In vivo Target Modulation and Biological Activity of CHIR-258, a Multitargeted Growth Factor Receptor Kinase Inhibitor, in Colon Cancer Models," *Clin. Cancer Res.*, May 15, 2005, vol. 11, No. 10; pp. 3633-3641.
List of compounds purchased from various vendors (3 pages).
Lopes De Menezes, D. E. et al., "CHIR-258: A Potent Inhibitor of FLT3 Kinase in Experimental Tumor Xenograft Models of Human Acute Myelogenous Leukemia," *Clin. Cancer Res.*, Jul. 15, 2005, vol. 11, No. 14, pp. 5281-5291.
Maguire, M.P., et al., "A New Series of PDGF Receptor Tyrosine Kinase Inhibitors: 3-Substituted Quinoline Derivatives," *J. Med. Chem.*, vol. 37, No. 14, pp. 2129-2137, 1994; published by American Chemical Society, Washington, D.C.
Matei, S., et al., "Condensation of ethyl 2-benzimidazoleacetate with carbonyl compounds," *Rev. Chim.*, vol. 33, No. 6, pp. 527-530, 1989, published by the Central Institute of Chemistry, Bucharest, Romania.
Parham, W. E. et al., "Elaboration of Bromoarylnitriles," *J. Org. Chem.*, vol. 41, No. 7, 1976, pp. 1187-1191.
Schäfer, H. et al., "Zur Synthese von 4-Aminochinolinen und -chinolinonen-(2) aus Anthranilsäurenitril," *Journal f. prakt. Chemie*, Band 321, Heft 4, 1979, pp. 695-698, Eng. Abstract included.
Smolich, B.D. et al., "The antiangiogenic protein kinase inhibitors SU5416 and SU6668 inhibit the SCF receptor (c-kit) in a human myeloid leukemia cell line and in acute myeloid leukemia blasts," *Blood*, vol. 97, No. 5, pp. 1413-1421, Mar. 1, 2001; published by The American Society of Hematology.
Trudel, S. et al., "CHIR-258, a novel, multitargeted tyrosine kinase inhibitor for the potential treatment of t(4;14) multiple myeloma," Blood, Apr. 1, 2005, vol. 105, No. 7, pp. 2941-2948.
Ukrainets, I., "Effective Synthesis of 3-(Benzimidazol-2-yl)-4-Hydroxy-2-Oxo-1,2-Dihydroquinolines," *Tet. Lett.*, vol. 36, No. 42, pp. 7747-7748, 1995, published by Elsevier Science Ltd., Great Britain.
Ukrainets, I., et al., "2-Carbethoxymethyl-4H-3,1-Benzoxazin-4-One. 3.*Condensation of o-Phenylenediamine," pp. 198-200, translated from *Khimiya Geterotsiklicheskikh Soedinii*, No. 2, pp. 239-241, Feb. 1992, published by Plenum Publ. Corp., London, Great Britain.
Ukrainets, I., et al., "4-Hydroxy-2-Quinolones 7.* Synthesis and Biological Properties of 1-R-3-(2-Benzimidazolyl)-4-Hydroxy-2-Quinolones," pp. 92-94, translated from *Khimiya Geterotsiklicheskikh Soedinii*, No. 1, pp. 105-108, Jan. 1993, published by Plenum Publ. Corp., London, Great Britain.
Ukrainets, I., et al., "4-Hydroxy-2-Quinolones. 16.* Condensation of N-R-Substituted Amides of 2-Carboxy-Malonanilic Acid With o-Phenylenediamine," pp. 941-944, translated from *Khimiya Geterotsiklicheskikh Soedinii*, vol. 8, pp. 1105-1108, Aug. 1993, published by Plenum Publ. Corp., London, Great Britain.

Ukrainets, I., et al., "4-Hydroxy-2-Quinolones. 32.* Synthesis and Antithyroid Activity of Thio Analogs of 1H-2-OXO-3-(2-Benzimidazolyl)-4-HydroxyQuinoline," *Chem. Heterocyclic Comp.*, vol. 33, No. 5, pp. 600-604, 1997, published by Kluwer Academic Publishers, London, Great Britain.

Veronese, A. C. et al., "Tin (IV) Chloride-promoted Synthesis of 4-Aminopyridines and 4-Aminoquinolines," *Tetrahedron*, vol. 51, No. 45, 1995, pp. 12277-12284; published by Elsevier Science Ltd.

Veronese, A. C. et al., "Tin(IV) Choloride-promoted vs. Metal β-Carbonyl-enolate-catalysed Reactions of β-Dicarbonyls with Nitriles," *J. Chem Research(S)*, 1988, pp. 246-247.

Wedge, S. R. et al., "ZD6474 Inhibits Vascular Endothelial Growth Factor Signaling Angiogenesis, and Tumor Growth following Oral Administration," *Cancer Research*, vol. 62, pp. 4645-4655, Aug. 15, 2002.

European Supplementary Search Report for Application No. EP 06 76 0144 dated Oct. 7, 2009.

Yu-Hua, Ji, et al., "tris-benzimidazole Derivatives: Design, Synthesis and DNA Sequence Recognition" Bioorganic & Medicinal Chemistry, vol. 9, 2001, pp. 2905-2919.

* cited by examiner

METHODS FOR SYNTHESIZING HETEROCYCLIC COMPOUNDS

FIELD OF THE INVENTION

This invention pertains generally to methods of synthesizing quinolinone compounds. More specifically, the invention described herein pertains to improved methods of synthesizing amino quinolinone compounds, and to methods for synthesizing amino quinolinone compounds and compositions that contain low quantities of lithium.

BACKGROUND OF THE INVENTION

A variety of chemical compounds and compositions have been reported as having activity against one or more vascular endothelial growth factor receptor tyrosine kinase (VEGF-RTK). Examples include quinoline derivatives such as described in WO 98/13350, aminonicotinamide derivatives (see, e.g. WO 01/55114), antisense compounds (see, e.g. WO 01/52904), peptidomimetics (see, e.g. WO 01/52875), quinazoline derivatives (see, e.g. U.S. Pat. No. 6,258,951) monoclonal antibodies (see, e.g. EP 1 086 705 A1), various 5,10,15,20-tetraaryl-porphyrins and 5,10,15-triaryl-corroles (see, e.g. WO 00/27379), heterocyclic alkanesulfonic and alkane carboxylic acid derivatives (see, e.g. DE19841985), oxindolylquinazoline derivatives (see, e.g. WO 99/10349), 1,4-diazaanthracine derivatives (see, e.g. U.S. Pat. No. 5,763,441), and cinnoline derivatives (see, e.g. WO 97/34876), and various indazole compounds (see, e.g. WO 01/02369 and WO 01/53268).

The synthesis of 4-hydroxy quinolone and 4-hydroxy quinoline derivatives is disclosed in a number of references. For example, Ukrainets et al. have disclosed the synthesis of 3-(benzimidazol-2-yl)-4-hydroxy-2-oxo-1,2-dihydroquinoline. Ukrainets, I. et al., Tetrahedron Lett. 42, 7747-7748 (1995); Ukrainets, I. et al., Khimiya Geterotsiklicheskikh Soedinii, 2, 239-241 (1992). Ukrainets has also disclosed the synthesis, anticonvulsive and antithyroid activity of other 4-hydroxy quinolones and thio analogs such as 1H-2-oxo-3-(2-benzimidazolyl)-4-hydroxyquinoline. Ukrainets, I. et al., Khimiya Geterotsiklicheskikh Soedinii, 1, 105-108 (1993); Ukrainets, I. et al., Khimiya Geterotsiklicheskikh Soedinii, 8, 1105-1108 (1993); Ukrainets, I. et al., Chem. Heterocyclic Comp. 33, 600-604, (1997).

The synthesis of various quinoline derivatives is disclosed in WO 97/48694. These compounds are disclosed as capable of binding to nuclear hormone receptors and being useful for stimulating osteoblast proliferation and bone growth. The compounds are also disclosed as being useful in the treatment or prevention of diseases associated with nuclear hormone receptor families.

Various quinoline derivatives in which the benzene ring of the quinoline is substituted with a sulfur group are disclosed in WO 92/18483. These compounds are disclosed as being useful in pharmaceutical formulations and as medicaments.

Quinolone and coumarin derivatives have been disclosed as having use in a variety of applications unrelated to medicine and pharmaceutical formulations. References that describe the preparation of quinolone derivatives for use in photopolymerizable compositions or for luminescent properties include: U.S. Pat. No. 5,801,212 issued to Okamoto et al.; JP 8-29973; JP 7-43896; JP 6-9952; JP 63-258903; EP 797376; and DE 23 63 459.

A plethora of substituted quinolinone compounds including quinolinone benzimidazolyl compounds and 4-amino substituted quinolinone benzimidazolyl compounds such as 4-amino-5-fluoro-3-[5-(4-methylpiperazin-1-yl)-1H-benzimidazol-2-yl]quinolin-2(1H)-one have recently been disclosed in references such as WO 02/22598 and WO 2004/043389. Such compounds are disclosed as inhibiting VEGF-RTKs. Such compounds are also disclosed in published United States patent applications U.S. 2002/0107392 and U.S. 2003/0028018 and U.S. Pat. Nos. 6,605,617, 6,774,237, and 6,762,194. Heterocyclic compounds related to benzimidazolyl quinolinones have recently been disclosed in WO 02/18383, U.S. 2002/0103230, and U.S. Pat. No. 6,756,383. Other such compounds are disclosed along with new uses of such compounds in inhibiting serine/threonine kinases and tyrosine kinases are disclosed in WO 2004/018419, and U.S. 2004/0092535, filed on Aug. 19, 2003, and claiming priority to each of the following provisional applications: U.S. Provisional Application No. 60/405,729 filed on Aug. 23, 2002; U.S. Provisional Application No. 60/426,107 filed on Nov. 13, 2002; U.S. Provisional Application No. 60/426,226 filed on Nov. 13, 2002; U.S. Provisional Application No. 60/426,282 filed on Nov. 13, 2002; U.S. Provisional Application No. 60/428,210 filed on Nov. 21, 2002; U.S. Provisional Application No. 60/460,327 filed on Apr. 3, 2003; U.S. Provisional Application No. 60/681,893 filed on May 17, 2005; U.S. Provisional Application No. 60/460,493 filed on Apr. 3, 2003; U.S. Provisional Application No. 60/478,916 filed on Jun. 16, 2003; and U.S. Provisional Application No. 60/484,048 filed on Jul. 1, 2003. Each of the references in this paragraph is hereby incorporated by reference in its entirety and for all purposes as if fully set forth herein.

Various methods for synthesizing amino benzimidazole quinolinone compounds are disclosed in U.S. patent application Ser. No. 10/982,757, filed on Nov. 5, 2004, which is hereby incorporated by reference in its entirety and for all purposes as if specifically set forth herein.

Although various methods have been disclosed for synthesizing quinolinone compounds, new methods which optimize yields of these compounds are needed because of their important applications in pharmaceutical formulations and applications.

SUMMARY OF THE INVENTION

The present invention provides methods of synthesizing heterocyclic compounds useful in the synthesis of amino substituted benzimidazolyl quinolinone compounds.

In one aspect, the present invention provides a method of synthesizing a compound of Formula VIH:

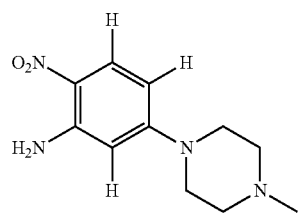

VIH

The method includes reacting 1-methylpiperazine with 5-halo-2-nitroaniline at an internal temperature sufficient to provide the compound of Formula VIH. In such aspects of the method, the 1-methylpiperazine and the 5-halo-2-nitroaniline are reacted in a solvent that comprises water. The water may be present in an amount greater than 50 percent by volume based on the amount of the solvent. In some embodiments, the 5-halo-2-nitroaniline is 5-chloro-2-nitroaniline, and in other embodiments is 5-fluoro-2-nitroaniline.

In some embodiments, the solvent comprises water in an amount greater than 80 percent by volume based on the amount of the solvent. In some such embodiments, the solvent comprises water in an amount greater than 90 percent by volume based on the amount of the solvent. In still further such embodiments, the solvent comprises water in an amount greater than 98 percent by volume based on the amount of the solvent. In still further such embodiments, the solvent consists essentially of or consists of water. In still other such embodiments, the solvent consists essentially of or consists of de-ionized or distilled water.

In some embodiments, the solvent is an aqueous solution comprising a salt such as NaCl. In some such embodiments, the concentration of the salt in the aqueous solutions ranges from about 1 to about 5 M. In some such embodiments, the concentration of the salt ranges from about 2 to about 5 M, in other embodiments ranges from about 3 to about 4.5 M, and in other embodiments ranges from about 3.5 to about 4.2M. In still other embodiments, the aqueous solution is saturated with a salt such as NaCl.

In some embodiments of methods for synthesizing a compound of Formula VIH, the solvent comprises a salt and an inorganic base. As in other methods described herein, the salt can be NaCl, but is not so limited. The concentration of the salt in the aqueous solution can range from about 1 to about 5 M, from about 2 to about 5 M, from about 3 to about 5 M, or as described above. Suitable inorganic bases for use in the methods include NaOH, KOH, $Ca(OH)_2$, $Mg(OH)_2$, $Na_2CO_3$, $K_2CO_3$, $K_3PO_4$, or mixtures of any two or more thereof. The amount of inorganic base used in some embodiments can range from about 0.5 to about 4 equivalents based on the amount of 5-halo-2-nitroaniline. In other embodiments, the amount of inorganic base is about 1 to about 4 equivalents, about 1 to about 3 equivalents, about 1.5 to about 2.5 equivalents or about 2 equivalents.

In some embodiments, the internal temperature is greater than about 95° C. In various such embodiments, the internal temperature ranges from about 99° C. to about 115° C., from about 100° C. to about 110° C., from about 105° C. to about 115° C., or from about 105° C. to about 110° C.

In some embodiments, the 1-methylpiperazine and the 5-halo-2-nitroaniline are reacted at the internal temperature for a reaction time of less than 20 hours. In some such embodiments, the reaction time is less than 10 hours. In some such embodiments, the reaction time is less than 8 hours.

In some embodiments, the molar ratio of the 1-methylpiperazine to the 5-halo-2-nitroaniline ranges from about 2:1 to about 10:1 at the start of the reaction. In some such embodiments, the molar ratio of the 1-methylpiperazine to the 5-halo-2-nitroaniline ranges from about 3:1 to about 4.5:1 at the start of the reaction. In still other such embodiments, the molar ratio of the 1-methylpiperazine to the 5-halo-2-nitroaniline ranges from about 4:1 to about 4.3:1 at the start of the reaction. An advantage of those methods utilizing a salt and an inorganic base is that less 1-methylpiperazine is needed to produce high yields of the product VIH than is needed without the inorganic base. For example, 1-methylpiperazine and 5-halo-2-nitroaniline can be present at a molar ratio ranging from about 1.5:1 to about 3:1.

In some embodiments, the yield of the compound of Formula VIH based on the amount of 5-halo-2-nitroaniline is greater than 90 percent. In other embodiments, the yield is greater than 93 percent. In still other embodiments, the yield is greater than 96 percent.

In another aspect, there are provided methods for synthesizing a heterocyclic compound, including reacting a mixture of 1-methylpiperazine and 5-halo-2-nitroaniline in a first solvent and at a first temperature sufficient to provide a compound of Formula VIH in the first solvent, wherein the first solvent is an organic solvent; adding to the mixture a volume of a second solvent, different from the first solvent; and forming a slurry of the compound of Formula VIH. The first solvent can comprise an alcohol. For example, the first solvent can comprise, consist essentially of, or consist of ethanol. In some embodiments, the first temperature sufficient to provide the compound of Formula VIH can range from about 90° C. to about 110° C. In certain embodiments, the 1-methylpiperazine and the 5-halo-2-nitroaniline are present at a molar ratio ranging from about 2:1 to about 5:1. In some embodiments, the 5-halo-2-nitroaniline is 5-chloro-2-nitroaniline, and in other embodiments, is 5-fluoro-2-nitroaniline.

In some embodiments of methods for synthesizing a heterocyclic compound, the second solvent comprises, consists essentially of, or consists of water. Such methods may further include cooling the mixture containing the compound of Formula VIH to a second temperature not less than 80% of the first temperature before the volume of water is added, and wherein the water is heated to about the second temperature before addition. For example, the second temperature can range from about 85° C. to about 95° C. In some embodiments, the slurry is formed by cooling the reaction mixture to a third temperature (e.g., from about 15° C. to about 25° C.) to induce formation of a slurry of the compound of Formula VIH.

In other embodiments of methods for synthesizing a heterocyclic compound, the second solvent is an organic solvent, the second solvent comprises, consists essentially of, or consists of heptane. In some embodiments, the methods further comprise cooling the mixture containing the compound of Formula VIH to a second temperature not lets than 70% of the first temperature, e.g. about 70° C. to about 85° C., before the volume of second solvent is added. As above, the slurry is formed by cooling the reaction mixture to a third temperature such as from about 15° C. to about 25° C. to induce formation of a slurry of the compound of Formula VIH. The methods may further include adding a second volume of a second organic solvent during cooling to the third temperature to form crystals of the compound of Formula VIH. The crystals of compound VIH may be collected and washed with water.

In another aspect, the invention provides methods for synthesizing a heterocyclic compound through more efficient use of 1-methylpiperazine by separating the product from the reaction solution and reusing the remaining reaction solution. Thus, the methods include reacting 1-methylpiperazine with 5-halo-2-nitroaniline in a solvent comprising water and a salt, to give a first reaction mixture, at a temperature sufficient to provide a compound of Formula VIH. The first reaction mixture may be cooled and filtered to give a first filtered solid comprising the compound of Formula VIH and a first filtrate comprising the solvent. The reaction may be carried out a second time by adding to the first filtrate 1-methylpiperazine, 5-halo-2-nitroaniline, and an amount of a base sufficient to neutralize any HCl in the first filtrate, to give a second reaction mixture, at a temperature sufficient to provide the compound of Formula VIH. Again, the second reaction mixture is cooled and filtered to provide a second filtered solid comprising the compound of Formula VIH and a second filtrate comprising the solvent. The methods may further include adding to the second filtrate, 1-methylpiperazine, 5-halo-2-nitroaniline, and an amount of a base sufficient to neutralize any HCl in the second filtrate, to give a third reaction mixture, at a temperature sufficient to provide the compound of Formula VIH. The third reaction mixture may be cooled and filtered to give a third filtered solid comprising the compound of Formula VIH and a third filtrate comprising the solvent. In some embodiments, the salt is NaCl. In other embodiments, the base is NaOH or KOH. Temperature for the reaction solution my range, e.g., from about 95° C. to about 120° C. In some embodiments, the 5-halo-2-nitroaniline is 5-chloro-2-nitroaniline, and in other embodiments, is 5-fluoro-2-nitroaniline.

In another aspect, the present invention provides a method of synthesizing a compound of Formula VIH, including reacting 1-methylpiperazine with 5-halo-2-nitroaniline at an internal temperature sufficient to provide the compound of Formula VIH. The 1-methylpiperazine and the 5-halo-2-nitroaniline are reacted in a solvent that comprises an organic solvent component that has a boiling point of greater than about 100° C. at atmospheric pressure. In some embodiments, the 5-halo-2-nitroaniline is 5-chloro-2-nitroaniline, and in other embodiments, is 5-fluoro-2-nitroaniline.

In some embodiments, the solvent is a compound of Formula HO—$(CH_2)_q$—OH or HO—$CH_2CH_2OCH_2CH_2$—OH, wherein q is selected from 2, 3, or 4. In some such embodiments, the solvent comprises propylene glycol or ethylene glycol. In still further such embodiments, the solvent consists essentially of or consists of propylene glycol or ethylene glycol. In still further such embodiments, the solvent consists essentially of or consists of ethylene glycol.

In some embodiments, the internal temperature is greater than about 95° C. In various such embodiments, the internal temperature ranges from about 99° C. to about 130° C., from about 115° C. to about 130° C., or from about 120° C. to about 125° C.

In some embodiments, the 1-methylpiperazine and the 5-chloro-2-nitroaniline are reacted at the internal temperature for a reaction time of less than 20 hours. In some such embodiments, the reaction time is less than 10 hours. In some such embodiments, the reaction time is less than 8 hours. In still other embodiments, the reaction time ranges from 3-6 hours, and in some embodiments ranges from 4-5 hours.

In some embodiments, the molar ratio of the 1-methylpiperazine to the 5-halo-2-nitroaniline ranges from about 2:1 to about 10:1 at the start of the reaction. In some such embodiments, the molar ratio of the 1-methylpiperazine to the 5-halo-2-nitroaniline ranges from about 3:1 to about 4.5:1 at the start of the reaction. In still other such embodiments, the molar ratio of the 1-methylpiperazine to the 5-halo-2-nitroaniline ranges from about 4:1 to about 4.3:1 at the start of the reaction.

In some embodiments, the yield of the compound of Formula VIH based on the amount of 5-halo-2-nitroaniline is greater than about 90 percent. In other embodiments, the yield is greater than about 92 percent. In still other embodiments, the yield is greater than about 96 percent.

As will be understood by those of skill in the art, the compound having formula VIH and methods of making this compound may be incorporated into any of the synthetic schemes described herein. For example, in some aspects, methods of the invention further include reducing a compound having the formula VIH, to produce the compound having the formula IVA

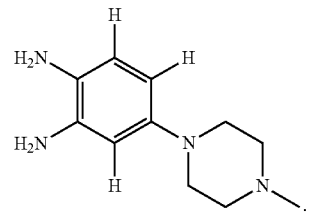

IVA

In other embodiments, the methods further include reacting a compound having the formula IVA with a compound having the formula V to prepare a compound of formula IIC or IID, wherein the compound having the formula V has the following structure,

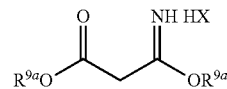

V wherein each $R^{9a}$ is independently an unsubstituted alkyl group having from 1 to 8 carbon atoms, and X is a halogen atom selected from F, Cl, Br, or I, or is the conjugate base of an acid; and the compound having the formula IIC or IID has the following structures,

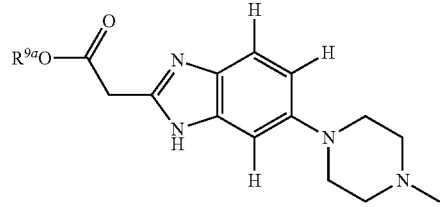

IIC

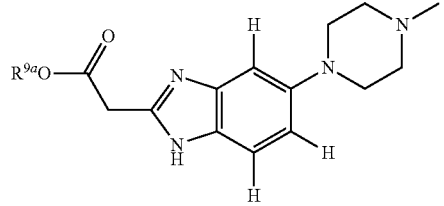

IID

In some embodiments, $R^{9a}$ is methyl or ethyl, and X is Cl.

In still other embodiments, the methods further comprise reacting a compound having the formula I with the compound having the formula IIC or IID in a suitable solvent in the presence of a sodium or potassium salt of a base to provide a reaction product comprising a benzimidazolyl quinolinone compound, wherein the compound of formula I has the following structure

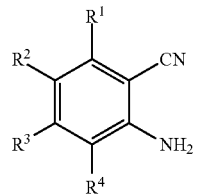

I wherein

R$^1$, R$^2$, R$^3$, and R$^4$ may be the same or different and are independently selected from H, Cl, Br, F, I, —OR$^{10}$ groups, —NR$^{11}$R$^{12}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, or substituted or unsubstituted heterocyclylalkyl groups; and further wherein, the benzimidazolyl compound is a compound having the formula IIIC, is a tautomer of the compound having the formula IIIC, is a salt of the compound having the formula III, or is a salt of the tautomer of the compound having the formula IIIC

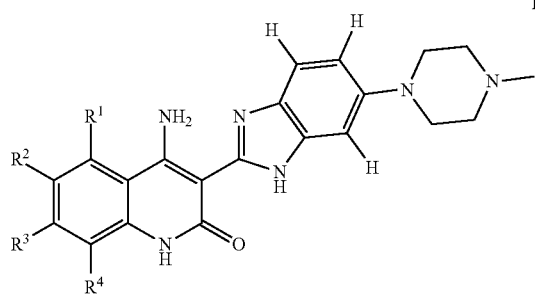

IIIC

In some embodiments of the methods, R$^1$ is selected from H, Cl, Br, F, or I. In other embodiments, R$^1$ is F. In still others, R$^2$, R$^3$, and R$^4$ are all H. In some embodiments of the methods, the compound of formula I is a compound of formula IA having the following structure

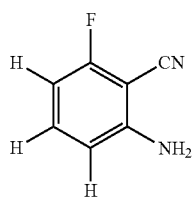

IA and the benzimidazolyl quinolinone compound is a compound having the formula IIIB, is a tautomer of the compound having the formula IIIB, is a salt of the compound having the formula IIIB, or is a salt of the tautomer of the compound having the formula IIIB

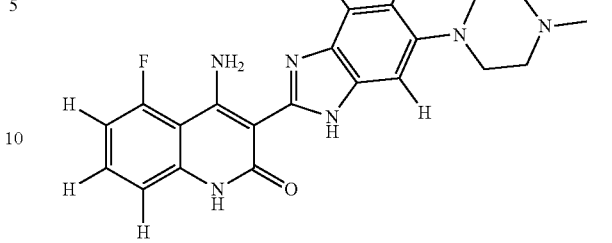

IIIB

Such methods can further include reacting the benzimidazolyl quinolinone compound with lactic acid to provide the lactic acid salt of the benzimidazolyl quinolinone compound.

Further objects, features and advantages of the invention will be apparent from the following detailed description.

DETAILED DESCRIPTION OF THE INVENTION

The present invention provides methods for synthesizing amino substituted quinolinone compounds. Such compounds act as antagonists of receptor tyrosine kinases, and, more particularly, as inhibitors of PDGFRα and PDGFRβ, bFGF and/or VEGF-RTK function. Such compounds also have potent activity with respect to other tyrosine kinases and also with respect to various serine/threonine kinases. The compounds provided herein can be formulated into pharmaceutical formulations that are useful, for example, in treating patients with a need for an inhibitor of VEGF-RTK, especially; for use in compositions and methods for reducing capillary proliferation and in the treatment of cancer. The methods for synthesizing amino substituted quinolinone compounds allows for the synthesis of formulations and compounds that have reduced amounts of lithium.

The following abbreviations and definitions are used throughout this application:

"bFGF" is an abbreviation that stands for basic fibroblast growth factor.

"bFGFR", also referred to as FGFR1, is an abbreviation that stands for a tyrosine kinase that interacts with the fibroblast growth factor FGF.

"PDGF" is an abbreviation that stands for platelet derived growth factor. PDGF interacts with tyrosine kinases PDGFRα and PDGFRβ.

"RTK" is an abbreviation that stands for receptor tyrosine kinase.

"Slurry" as used herein refers to a mixture comprising insoluble particles in a liquid.

"VEGF" is an abbreviation that stands for vascular endothelial growth factor.

"VEGF-RTK" is an abbreviation that stands for vascular endothelial growth factor receptor tyrosine kinase.

Generally, reference to a certain element such as hydrogen or H is meant to include all isotopes of that element. For example, if an R group is defined to include hydrogen or H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH $-CH(CH_3)_2$, $-CH(CH_3)(CH_2CH_3)$, $-CH(CH_2CH_3)_2$, $-C(CH_3)_3$, $-C(CH_2CH_3)_3$, $-CH_2CH(CH_3)_2$, $-CH_2CH(CH_3)(CH_2CH_3)$, $-CH_2CH(CH_2CH_3)_2$, $-CH_2C(CH_3)_3$, $-CH_2C(CH_2CH_3)_3$, $-CH(CH_3)CH(CH_3)(CH_2CH_3)$, $-CH_2CH_2CH(CH_3)_2$, $-CH_2CH_2CH(CH_3)(CH_2CH_3)$, $-CH_2CH_2CH(CH_2CH_3)_2$, $-CH_2CH_2C(CH_3)_3$, $-CH_2CH_2C(CH_2CH_3)_3$, $-CH(CH_3)CH_2CH(CH_3)_2$, $-CH(CH_3)CH(CH_3)CH(CH_3)_2$, $-CH(CH_2CH_3)CH(CH_3)CH(CH_3)(CH_2CH_3)$, and others. The phrase also includes cyclic alkyl groups such as cycloalkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and $-CH(CH_3)_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted aryl" refers to aryl groups that do not contain heteroatoms. Thus, by way of example, the phrase includes, but is not limited to, groups such as phenyl, biphenyl, anthracenyl, and naphthyl. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. In some embodiments, unsubstituted aryl groups have from 6 to 14 carbon atoms. Unsubstituted aryl groups may be bonded to one or more carbon atom(s), oxygen atom(s), nitrogen atom(s), and/or sulfur atom(s) in the parent compound.

The phrase "substituted aryl group" has the same meaning with respect to unsubstituted aryl that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to groups such as tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, $-CH=C(H)(CH_3)$, $-CH=C(CH_3)_2$, $-C(CH_3)=C(H)_2$, $-C(CH_3)=C(H)(CH_3)$, $-C(CH_2CH_3)=CH_2$, cyclohexenyl, cyclopentenyl, cyclohexadienyl, butadienyl, pentadienyl, and hexadienyl among others. In some embodiments, unsubstituted alkenyl groups have from 2 to 8 carbon atoms.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms. Examples include, but are not limited to $-C\equiv C(H)$, $-C\equiv C(CH_3)$, $-C\equiv C(CH_2CH_3)$, $-C(H_2)C\equiv C(H)$, $-C(H)_2C\equiv C(CH_3)$, and $-C(H)_2C\equiv C(CH_2CH_3)$ among others. In some embodiments, unsubstituted alkynyl groups have from 2 to 8 carbon atoms.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxolyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiophene, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isooxazole, furan, and tetrahydrofuran.

The phrase "substituted heterocyclyl" refers to an unsubstituted heterocyclyl group as defined above in which one or more of the ring members is bonded to a non-hydrogen atom such as described above with respect to substituted alkyl groups and substituted aryl groups. Examples, include, but are not limited to, 2-methylbenzimidazolyl, 5-methyl benzimidazolyl, 5-chlorobenzthiazolyl, N-alkyl piperazinyl groups such as 1-methyl piperazinyl, piperazine-N-oxide, N-alkyl piperazine N-oxides, 2-phenoxy-thiophene, and 2-chloropyridinyl among others. In addition, substituted heterocyclyl groups also include heterocyclyl groups in which the bond to the non-hydrogen atom is a bond to a carbon atom that is part of a substituted and unsubstituted aryl, substituted and unsubstituted aralkyl, or unsubstituted heterocyclyl group. Examples include but are not limited to 1-benzylpiperidinyl, 3-phenylhiomorpholinyl, 3-(pyrrolidin-1-yl)-pyrrolidinyl, and 4-(piperidin-1-yl)-piperidinyl. Groups such as N-alkyl substituted piperazine groups such as N-methyl piperazine, substituted morpholine groups, and piperazine N-oxide groups such as piperazine N-oxide and N-alkyl piperazine N-oxides are examples of some substituted heterocyclyl groups. Groups such as substituted piperazine groups such as N-alkyl substituted piperazine groups such as N-methyl piperazine and the like, substituted morpholine groups, piperazine N-oxide groups, and N-alkyl piperazine N-oxide groups are examples of some substituted heterocyclyl groups that are especially suited as $R^6$ or $R^7$ groups.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—$CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. In addition, substituted heterocyclylalkyl group also includes groups in which a carbon bond or a hydrogen bond of the alkyl part of the group is replaced by a bond to a substituted and unsubstituted aryl or substituted and unsubstituted aralkyl group. Examples include but are not limited to phenyl-(piperidin-1-yl)-methyl and phenyl-(morpholin-4-yl)-methyl.

The phrase "unsubstituted alkoxy" refers to a hydroxyl group (—OH) in which the bond to the hydrogen atom is replaced by a bond to a carbon atom of an otherwise unsubstituted alkyl group as defined above.

The phrase "substituted alkoxy" refers to a hydroxyl group (—OH) in which the bond to the hydrogen atom is replaced by a bond to a carbon atom of an otherwise substituted alkyl group as defined above.

The phrase "unsubstituted heterocyclyloxy" refers to a hydroxyl group (—OH) in which the bond to the hydrogen atom is replaced by a bond to a ring atom of an otherwise unsubstituted heterocyclyl group as defined above.

The phrase "substituted heterocyclyloxy" refers to a hydroxyl group (—OH) in which the bond to the hydrogen atom is replaced by a bond to a ring atom of an otherwise substituted heterocyclyl group as defined above.

The phrase "unsubstituted aryloxyalkyl" refers to an unsubstituted alkyl group as defined above in which a carbon bond or hydrogen bond is replaced by a bond to an oxygen atom which is bonded to an unsubstituted aryl group as defined above.

The phrase "substituted aryloxyalkyl" refers to an unsubstituted aryloxyalkyl group as defined above in which a bond to a carbon or hydrogen group of the alkyl group of the aryloxyalkyl group is bonded to a non-carbon and non-hydrogen atom as described above with respect to substituted alkyl groups or in which the aryl group of the aryloxyalkyl group is a substituted aryl group as defined above.

The phrase "unsubstituted heterocyclyloxyalkyl" refers to an unsubstituted alkyl group as defined above in which a carbon bond or hydrogen bond is replaced by a bond to an oxygen atom which is bonded to an unsubstituted heterocyclyl group as defined above.

The phrase "substituted heterocyclyloxyalkyl" refers to an unsubstituted heterocyclyloxyalkyl group as defined above in which a bond to a carbon or hydrogen group of the alkyl group of the heterocyclyloxyalkyl group is bonded to a non-carbon and non-hydrogen atom as described above with respect to substituted alkyl groups or in which the heterocyclyl group of the heterocyclyloxyalkyl group is a substituted heterocyclyl group as defined above.

The phrase "unsubstituted heterocyclylalkoxy" refers to an unsubstituted alkyl group as defined above in which a carbon bond or hydrogen bond is replaced by a bond to an oxygen atom which is bonded to the parent compound, and in which another carbon or hydrogen bond of the unsubstituted alkyl group is bonded to an unsubstituted heterocyclyl group as defined above.

The phrase "substituted heterocyclylalkoxy" refers to an unsubstituted heterocyclylalkoxy group as defined above in which a bond to a carbon or hydrogen group of the alkyl group of the heterocyclylalkoxy group is bonded to a non-carbon and non-hydrogen atom as described above with respect to substituted alkyl groups or in which the heterocyclyl group of the heterocyclylalkoxy group is a substituted heterocyclyl group as defined above. Further, a substituted heterocyclylalkoxy group also includes groups in which a carbon bond or a hydrogen bond to the alkyl moiety of the group may be substituted with one or more additional substituted and unsubstituted heterocycles. Examples include but are not limited to pyrid-2-ylmorpholin-4-ylmethyl and 2-pyrid-3-yl-2-morpholin-4-ylethyl.

The phrase "unsubstituted alkoxyalkyl" refers to an unsubstituted alkyl group as defined above in which a carbon bond or hydrogen bond is replaced by a bond to an oxygen atom which is bonded to an unsubstituted alkyl group as defined above.

The phrase "substituted alkoxyalkyl" refers to an unsubstituted alkoxyalkyl group as defined above in which a bond to a carbon or hydrogen group of the alkyl group and/or the alkoxy group of the alkoxyalkyl group is bonded to a non-carbon and non-hydrogen atom as described above with respect to substituted alkyl groups.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, lactic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

Unless otherwise indicated, the terms "temperature," "internal temperature," and "internal reaction temperature" all refer to the temperature of a reaction mixture in a reaction vessel. The temperature of a reaction mixture is not necessarily the same as the temperature of the reaction vessel containing the reaction mixture or the heat source used to heat the reaction mixture.

As used herein, the term "about" in conjunction with a given temperature, time, mass, molarity or molar ratio, refers to the value being within 10 percent of the given temperature, time mass, molarity or molar ratio. In some embodiments, "about" in conjunction with a given temperature refers to a temperature that is ±5° C. of the given temperature or ±2° C. of the given temperature in other embodiments. In instances where a value that is ±5° C. or ±2° C. of the given temperature is more than the 10 percent of the given temperature, it is intended that the larger range prevail.

Generally, the invention provides methods for synthesizing benzimidazolyl quinolinone compounds such as amino substituted benzimidazolyl quinolinone compounds. The invention further provides amino substituted benzimidazolyl quinolinone compounds and formulations that have reduced amounts of lithium and methods of synthesizing such compounds and compositions.

In one aspect, the present invention provides a method for synthesizing a substituted or unsubstituted 4-amino-3-benzimidazolyl quinolinone compound and compositions that include such a compound. The method includes reacting a first compound having the formula I with a second compound having the formula II in a suitable solvent in the presence of a sodium or potassium salt of a base. In some embodiments, the method includes reacting the first compound with the second compound in the suitable solvent in the presence of the potassium salt of the base. The reaction of the first compound with the second compound produces the substituted or unsubstituted 4-amino-3-benzimidazolyl quinolinone compound. Formula I and formula II have the following structures:

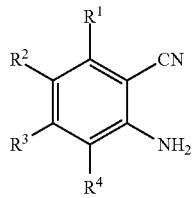

I

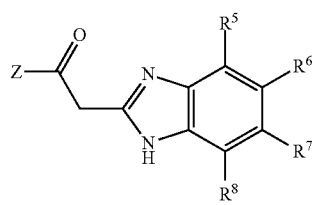

II where:

$R^1$, $R^2$, $R^3$, and $R^4$ may be the same or different and are independently selected from H, Cl, Br, F, I, —$OR^{10}$ groups, —$NR^{11}R^{12}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, or substituted or unsubstituted heterocyclylalkyl groups;

$R^5$, $R^6$, $R^7$, and $R^8$ may be the same or different and are independently selected from H, Cl, Br, F, I, —$OR^{13}$ groups, —$NR^{14}R^{15}$ groups, —$SR^{16}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted heterocyclylalkyl groups, substituted or unsubstituted alkoxyalkyl groups, substituted or unsubstituted aryloxyalkyl groups, or substituted or unsubstituted heterocyclyloxyalkyl groups;

Z is selected from —$OR^{9a}$ groups or —$NR^{9b}R^{9c}$ groups;

$R^{9a}$ is an unsubstituted alkyl group having from 1 to 8 carbon atoms and is absent if Z is a —$NR^{9b}R^{9c}$ group;

$R^{9b}$ and $R^{9c}$ are independently selected from unsubstituted alkyl groups having from 1 to 8 carbon atoms or are both absent if Z is a —$OR^{9a}$ group;

$R^{10}$ and $R^{13}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, substituted or unsubstituted alkoxyalkyl groups, substituted or unsubstituted aryloxyalkyl groups, or substituted or unsubstituted heterocyclyloxyalkyl groups;

$R^{11}$ and $R^{14}$ may be the same or different and are independently selected from substituted or unsubstituted alkyl groups, substituted or unsubstituted aryl groups, or substituted or unsubstituted heterocyclyl groups;

$R^{12}$ and $R^{15}$ may be the same or different and are independently selected from substituted or unsubstituted alkyl groups, substituted or unsubstituted aryl groups, or substituted or unsubstituted heterocyclyl groups; and $R^{16}$ is selected from substituted or unsubstituted alkyl groups, substituted or unsubstituted aryl groups, or substituted or unsubstituted heterocyclyl groups.

In some embodiments, the substituted or unsubstituted 4-amino-3-benzimidazolyl quinolinone compound is a compound having the formula III, is a tautomer of the compound having the formula III, is a salt of the compound having the formula III, or is a salt of the tautomer of the compound having the formula III. Formula III has the following structure:

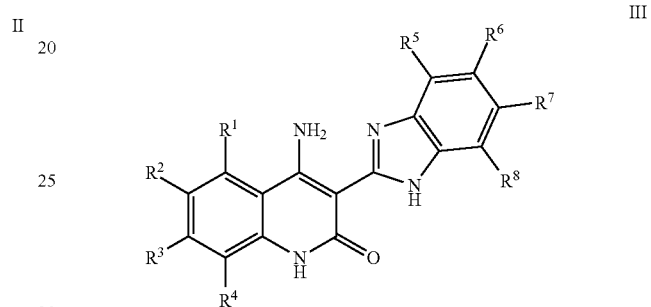

III where $R^1$ through $R^8$ and $R^{10}$ through $R^{16}$ have the values described above.

In some embodiments of the method, $R^1$ is selected from H, Cl, Br, F, or I. In some such embodiments, $R^1$ is F. In some specific embodiments, $R^1$ is F and each of $R^2$, $R^3$ and $R^4$ is H such that the first compound is a compound having the formula IA which has the following structure

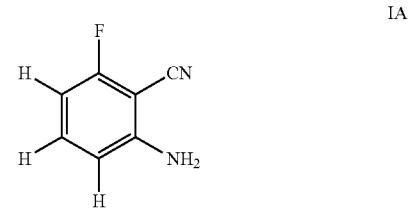

IA

In other embodiments, at least one of $R^6$ or $R^7$ is a substituted or unsubstituted heterocyclyl group. In some such embodiments, one of $R^6$ or $R^7$ is a heterocyclyl group and the other of $R^6$ or $R^7$ is a H. In some embodiments, one of $R^6$ or $R^7$ is a heterocyclyl group selected from a substituted or unsubstituted piperidinyl group, piperazinyl group, or morpholinyl group. In some such embodiments one of $R^6$ or $R^7$ is an N-alkyl piperazinyl group such as an N-methyl piperazinyl group or the like and, in some such embodiments, the other of $R^6$ or $R^7$ is a H. In other such embodiments, Z is an —$OR^{9a}$ group. Therefore, in some embodiments, the second compound is a compound having the formula IIA or IIB and has one of the following structures where $R^5$, $R^8$, and $R^{9a}$ have the values described above for compounds having the formula II.

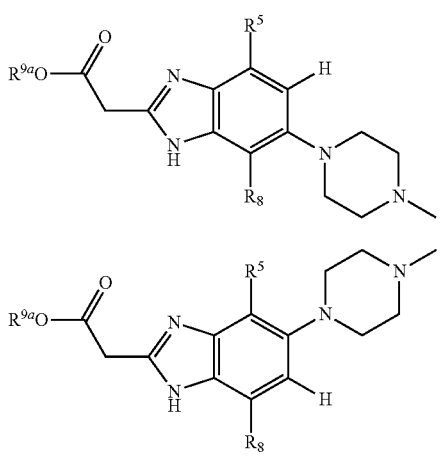

IIA

IIB

In some further embodiments, the second compound is a compound having the formula IIA or IIB and both $R^5$ and $R^8$ are H such that the second compound is a compound having the formula IIC or IID and has one of the following structures.

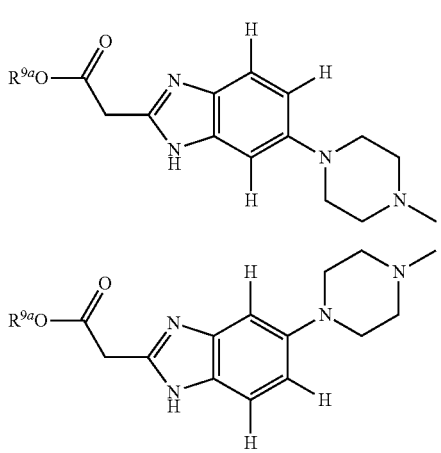

IIC

IID

In some embodiments of the method, $R^{9a}$, $R^{9b}$, and $R^{9c}$ are straight chain alkyl groups selected from methyl, ethyl, propyl, butyl, or pentyl groups or are branched chain alkyl groups selected from i-propyl, s-butyl, or t-butyl groups. In some embodiments, $R^{9a}$, $R^{9b}$, or $R^{9c}$ are methyl, ethyl, or propyl groups and in yet Other embodiments, $R^{9a}$, $R^{9b}$, or $R^{9c}$ are ethyl groups.

In some embodiments of the method, the method includes reacting the first compound with the second compound in a solvent such as a dialkyl ether such as, but not limited to, diethyl ether or the like; a cyclic ether such as, but not limited to, dioxane, tetrahydrofuran or the like; an aromatic solvent such as toluene, o-xylene, m-xylene, p-xylene, mixtures thereof, or the like; or combinations of these solvents. Other suitable solvents include polar aprotic solvents such as DMF (N,N-Dimethylformamide) and the like. In some such embodiments, the solvent is tetrahydrofuran. In other embodiments, the solvent is toluene. In some embodiments, the concentration of the first compound is greater than or about 0.10 M or is greater than or about 0.15 M based on the amount of the solvent when the first compound and the second compound are reacted. In some such embodiments, the concentration of the first compound ranges from about 0.10 M to about 0.30 M based on the amount of solvent when the first compound and the second compound are reacted. In some such embodiments, the concentration of the first compound ranges from about 0.15 M to about 0.25 M based on the amount of solvent when the first compound and the second compound are reacted. In some such embodiments, the concentration of the first compound ranges from about 0.17 M to about 0.22 M based on the amount of solvent when the first compound and the second compound are reacted. In some such embodiments, the concentration of the first compound is about 0.19 M based on the amount of solvent when the first compound and the second compound are reacted. In some such embodiments, the concentration of the first compound and/or the second compound ranges from about 0.15 M to about 0.50 M based on the amount of solvent when the first compound and the second compound are reacted. In some such embodiments, the concentration of the first compound and/or the second compound ranges from about 0.20 M to about 0.45 M based on the amount of solvent when the first compound and the second compound are reacted. In some such embodiments, the concentration of the first compound and/or the second compound ranges from about 0.25 M to about 0.45 M based on the amount of solvent when the first compound and the second compound are reacted. In some embodiments, the concentration of the second compound is greater than about 0.10 M based on the amount of the solvent when the first compound and the second compound are reacted. In other such embodiments, the concentration of the second compound is greater than about 0.15 M, whereas in other embodiments, the concentration of the second compound is greater than about 0.20 M based on the amount of solvent when the first compound and the second compound are reacted. In some embodiments, the concentration of the second compound ranges from about 0.15 M to about 0.30 M based on the amount of solvent when the first compound and the second compound are reacted. In some embodiments, the concentration of the second compound ranges from about 0.18 M to about 0.26 M based on the amount of solvent when the first compound and the second compound are reacted. In some embodiments, the concentration of the second compound ranges from about 0.20 M to about 0.24 M based on the amount of solvent when the first compound and the second compound are reacted. In some embodiments, the concentration of the second compound is about 0.22 M based on the amount of solvent when the first compound and the second compound are reacted. In some embodiments, the solvent is dried prior to use in the reaction. In some such embodiments, the solvent of the reaction comprises, less than 0.5 percent water, less than 0.25 percent water, less than 0.1 percent water, or is less than 0.05 percent water by weight. In still other such embodiments, the solvent comprises less than 0.01 percent water, or is less than 0.005 percent water based on the weight. In some embodiments, the solvent is dried prior to use in the reaction. In some embodiments, a mixture of the solvent and the second compound is dried prior to addition of the potassium or sodium salt of the base. In some such embodiments, the mixture of the solvent and the second compound comprises, less than 0.5 percent water, less than 0.25 percent water, less than 0.2 percent water, less than 0.1 percent water, or less than 0.05 percent water which may be determined by Karl Fischer analysis.

In some embodiments of the method, the method includes reacting the first compound with the second compound in the suitable solvent using the sodium or potassium salt of a base that may be used to generate an enolate anion, which, in some embodiments, may be a sterically-hindered base. As used herein, the term "base" refers to a chemical compound that deprotonates another compound when reacted with it. In some such embodiments, the sodium or potassium salt of the base that may be used to generate an enolate anion is a base such as, for example, NaH, KH, $Na_2CO_3$, $K_2CO_3$, sodium and potassium alkoxides such as, but not limited to, sodium and potassium t-butoxide, propoxide, propoxide, ethoxide, methoxide, and the like, sodium amide ($NaNH_2$), potassium amide ($KNH_2$), and the like. In some embodiments, the base is sodium or potassium t-butoxide, and in some such embodiments, the base is potassium t-butoxide in a solvent such as THF. In some of these embodiments the base is potassium t-butoxide (20% in THF). In some embodiments, the sterically hindered base is an amide anion and in some such embodiments, the amide nitrogen is bonded to two trialkylsilyl groups. In some such embodiments, the sodium or potassium salt of the base is selected from a sodium or potassium bis(trialkylsilyl)amide. In some such embodiments, the sodium or potassium bis(trialkylsilyl)amide is sodium bis(trimethylsilyl)amide (NaHMDS) or potassium bis(trimethylsilyl)amide (KHMDS). In some embodiments, the method further includes adding the sodium or potassium salt of the base to a mixture of the first compound and the second compound in the suitable solvent. In some embodiments, the sodium or potassium salt of the base is present in an amount of from 2 to 4 equivalents, and in some such embodiments in an amount of from 2.5 to 3 equivalents, with respect to the first compound. In still other embodiments, the sodium or potassium salt of the base is present in an amount of 2 to 4 equivalents, and in some such embodiments in an amount of from 2.5 to 3 equivalents, with respect to the second compound. In some embodiments, the second compound is present in an amount of from 1 to 2 equivalents with respect to the first compound. In some such embodiments, the second compound is present in an amount of from 1 to 1.5 equivalents with respect to the first compound.

In some embodiments of the method for synthesizing a substituted or unsubstituted 4-amino-3-benzimidazole quinolinone compound and compositions that include such compounds, the method includes adding the potassium salt of the base to a mixture comprising the first compound, the second compound, and the suitable solvent at a temperature of from about 20° C. to about 50° C. In some such embodiments, the potassium salt of the base is added to the mixture and the temperature of the mixture is from about 25° C. to about 45° C., from about 35° C. to about 45° C., or from about 38° C. to about 42° C. when the potassium salt of the base is first added to the mixture. In some embodiments, the internal temperature is 40° C. or about 40° C. when the potassium salt of the base is first added to the mixture. The internal reaction temperature generally increases, for example up to about 62° C. or about 65° C. upon addition of the potassium salt of the base to the reaction mixture. However, in some embodiments, the internal temperature is maintained at about 30° C. to about 52° C., about 36° C. to about 52° C., or in some embodiments from about 38° C. to about 50° C. during addition of the potassium salt of the base. In some such embodiments, the potassium salt of the base is added to the mixture over a period of from about 2 to about 20 minutes. In some such embodiments, the potassium salt of the base is added to the mixture over a period of from about 3 to about 10 minutes and in some such embodiments, the potassium salt of the base is added to the mixture over a period of from about 5 to about 10 minutes or in some embodiments over a period of about 5 minutes.

In some embodiments of the method for synthesizing a substituted or unsubstituted 4-amino-3-benzimidazole quinolinone compound and compositions that include such compounds, the method includes adding the sodium or potassium salt of the base to a mixture comprising the first compound, the second compound, and the suitable solvent at a temperature of from about 15° C. to about 50° C. In some such embodiments, the potassium salt of the base is added to the mixture and the temperature of the mixture is from about 15° C. to about 25° C., from about 15° C. to about 20° C., or from about 17° C. to about 20° C. when the potassium salt of the base is first added to the mixture. In some embodiments, the internal temperature is about 17° C. to about 20° C. when the potassium salt of the base is first added to the mixture. In some embodiments, the internal temperature is maintained at a temperature of less than or about 25° C. during addition of the base. In some such embodiments, the internal temperature of the reaction is raised to about 30° C. and the reaction is monitored for completion using HPLC.

In some embodiments, the method further includes (a) adding an aromatic solvent such as toluene to a reaction flask to provide a reaction mixture comprising the first compound and the second compound; (b) distilling at least a portion of the aromatic solvent from the reaction flask, and (c) repeating (a) and (b) until the water content is less than 0.1 percent, 0.05, 0.04 percent, or 0.03 percent which may be determined using Karl Fischer analysis. In some embodiments, the distillation may be conducted under reduced pressure. In some embodiments, the second compound is dried by (a) mixing the second compound with a suitable organic solvent such as THF, toluene, ethanol, or the like to form a solution, (b) concentrating the second compound by removing at least a portion of the solvent; and (c) optionally repeating steps (a) and (b) one or more additional times. In some such embodiments, (a) and (b) are repeated until the water content of the solution is less than 0.5%, less than 0.4%, less than 0.3%, less than 0.25%, less than 0.20%, less than 0.10%, less than 0.05%, or less than 0.03% which may be determined by Karl Fischer analysis. In some embodiments, steps (a) and (b) are accomplished at least four times. In some embodiments, the second compound may be dried in a reaction vessel and when the desired quantity of drying is achieved, such as a water level of less than 0.25% or less than 0.20%, the first compound and the potassium or sodium salt of the base are added to the reaction vessel. In such embodiments, solvents such as those suitable for use in the reaction of the first compound with the second compound may be used to dry the second compound. Such solvents include ethereal solvents such as diethyl ether, dioxane, THF, and the like and aromatic solvents such as toluene.

In some embodiments of the method for synthesizing a substituted or unsubstituted 4-amino-3-benzimidazolyl quinolinone compound and compositions that include such a compound, the method includes drying the second compound to a water level of less than 5.5 percent by weight prior to reacting it with the first compound or adding it to a reaction vessel containing the first compound or the suitable solvent. In some such embodiments, the second compound is dried to a water level of less than 5 percent by weight, less than 4 percent by weight, less than 3 percent by weight, less than 2.5 percent by weight, less than 2 percent by weight, less than 1 percent by weight, or less than 0.5 percent by weight. In some such embodiments, the second compound may be dried by mixing the hydrated second compound with an organic solvent such as THF, toluene, or ethanol to form a solution, concentrating the solution by solvent removal, and drying the resulting composition under vacuum with heating. In some such embodiments, the second compound is dried by: (a) mixing the hydrated second compound with an organic solvent such as THF, toluene, or ethanol to form a solution, (b)

concentrating the second compound by removing at least a portion of the solvent, (c) optionally repeating steps (a) and (b) one or more additional times, and then (d) drying the resulting composition under vacuum with heating.

In some embodiments of the method for synthesizing a substituted or unsubstituted 4-amino-3-benzimidazolyl quinolinone compound and compositions that include such a compound, the method includes reacting the first compound with the second compound in the presence of the sodium or potassium salt of the base for a period of time ranging from about 30 minutes to about 360 minutes, from about 120 minutes to about 300 minutes, from about 180 to about 300 minutes, from about 180 minutes to about 270 minutes, from about 210 minutes to about 270 minutes, or from about 210 minutes to about 240 minutes at a temperature suitable to provide the desired benzimidazolyl quinolinone compound. In some embodiments, the reaction product mixture of the substituted or unsubstituted 4-amino-3-benzimidazolyl quinolinone compound produced by the reaction of the first compound with the second compound is quenched by pouring the reaction product mixture into water. In other embodiments, water is added to the reaction mixture which, in some embodiments, is cooled to a temperature of from about 20° C. to about 35° C. or from about 20° C. to about 35° C. prior to adding the water. In some embodiments, solvent may be removed under vacuum after water is added and then additional water is added prior to collection of the solid by filtration. The quenched reaction product mixture is typically filtered and washed with water providing the 4-amino-3-benzimidazolyl quinolinone compound, and in some embodiments, the quenched reaction product may be cooled to a temperature of about 5° C. to about 10° C. prior to filtration although this is not necessary. In some embodiments, the collected product may be dried under vacuum to produce a yield of greater than about 30 percent, greater than about 40 percent, greater than about 50 percent, greater than about 60 percent, greater than about 70 percent, or greater than about 80 percent of the 4-amino-3-benzimidazolyl quinolinone compound. Some embodiments of the method may further include: (a) mixing the collected product with ethanol; (b) heating the ethanolic mixture for a period of from about 10 minutes to about 180 minutes, of from about 30 minutes to about 120 minutes, or of about 60 minutes at a temperature of from about 40° C. to about 78° C., of from about 45° C. to about 78° C., of from about 60° C. to about 78° C., or a reflux temperature; (c) cooling the mixture to a temperature of less than about 40° C., less than about 35° C., less than about 30° C., or less than about 20° C.; (d) and filtering the cooled mixture. However, it is not necessary that the mixture be cooled prior to filtration. In some such embodiments the filtered product may be washed with a solvent such as ethanol or water. The resulting product may be dried under vacuum with heating such as in a vacuum oven, a drying pistol, a rotary evaporator, or the like.

In some embodiments of the method for synthesizing a substituted or unsubstituted 4-amino-3-benzimidazolyl quinolinone compound and compositions that include such a compound, the method includes reacting a compound having the formula IV with a compound having the formula V to provide the second compound where the variables $R^5$, $R^6$, $R^7$, $R^8$, and $R^{9a}$ have the values set forth above with respect to the second compound having the formula II and X is a halogen atom such as F, Cl, Br, or I, or is the conjugate base of an acid.

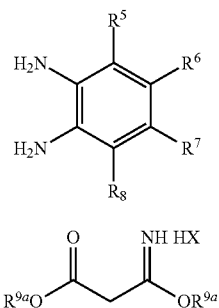

In some such embodiments, the compound having the formula IV has the formula IVA.

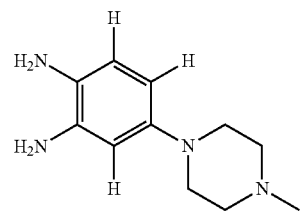

In some such embodiments, the compound having the formula V has the formula VA.

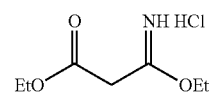

In some embodiments, the compound having the formula IV is reacted with the compound having the formula V in solvent such as an alcohol such as, but not limited to, ethanol at an internal temperature of from about 30° C. to about 70° C., of from about 35° C. to about 60° C., or of from about 40° C. to about 50° C. for a period of time of from about 45 minutes to about 240 minutes, of from about 60 minutes to about 180 minutes, or of from about 60 minutes to about 120 minutes. In some embodiments, the reaction product from the reaction of the compound having the formula IV with the compound having the formula V is cooled, for example to about 25° C. or the like, and is filtered. In other embodiments, the reaction product is still warm when it is filtered through a filter medium such as Celite. In some embodiments, the filter medium may be washed with a solvent such as ethanol, and the filtrate may be concentrated by solvent removal. The concentrated product may then be mixed with an aqueous HCl solution, in some embodiments, a 0.37 percent HCl solution and in other embodiments a 1M HCl solution A base such as NaOH, for example a 30% NaOH solution, may then be added in one portion or gradually such that a precipitate forms. In some embodiments, the reaction product may be mixed or dissolved with water, in some embodiments deionized water, that is neutral with respect to pH. In such embodiments, the resulting mixture is typically cooled to about 0° C. and then is made basic by addition of a base such as NaOH. In some such embodiments, the pH is brought to about 9.2 by addition of 20% NaOH. In some embodiments, the resulting mixture is stirred for a period of about 1 to about 5 hours, for example, for about 4 hours or the like, and is then filtered, washed with water and dried in a vacuum oven or the like.

In some embodiments of the method for synthesizing a substituted or unsubstituted 4-amino-3-benzimidazolyl quinolinone compound and compositions that include such a compound, a compound having the formula VIA, VIB, or mixtures thereof is reduced, typically catalytically as described below, with $H_2$ to produce the compound having the formula IV where the variables $R^5$, $R^6$, $R^7$, and $R^8$ have the values set forth above with respect to the second compound having the formula II.

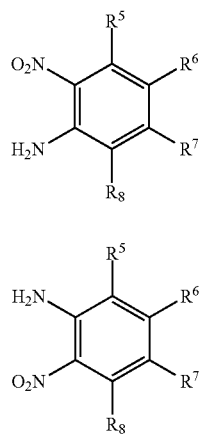

VIA

VIB

In some such embodiments, the compound having the formula VIA is a compound having the formula VIC or VID and/or the compound having the formula VIB is a compound having the formula VIE or VIF. In some such embodiments, $R^6$ or $R^7$ is a substituted or unsubstituted heterocyclyl group, that, in some embodiments is selected from substituted or unsubstituted piperidinyl groups, piperazinyl groups, or morpholinyl groups. In some such embodiments, one of $R^6$ or $R^7$ is an N-alkyl piperazinyl group such as an N-methyl piperazinyl group such that the compounds having the formula VIC, VID, VIE, and VIF have the formula VIG or VIH.

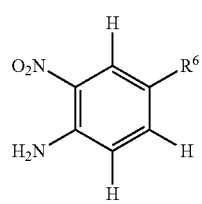

VIC

VID

VIE

VIF

VIG

VIH

In some embodiments, the compound reduced by $H_2$ is a compound having the formula VIH. In other embodiments, the compound reduced by $H_2$ is a compound having the formula VIG. In some embodiments, the compound having the formula VIA, VIB, or mixtures thereof is reduced with $H_2$ in an alcohol solvent such as ethanol using a transition metal hydrogenation catalyst such as palladium on carbon (Pd/C). In some embodiments, the Pd/C is 5 percent Pd/C and in some embodiments, the Pd/C is 5 percent Pd/C with 50 percent water on a weight by weight basis. In some embodiments, the reaction is conducted at an internal temperature of from about 25° C. to about 70° C., from about 30° C. to about 60° C., or in some embodiments from about 40° C. to about 55° C. or from about 45° C. to about 55° C. for a period of time of from about 1 to about 12 hours, of from about 3 to about 10 hours, of from about 4 to about 8 hours, or of about 6 hours. In some embodiments, the reduced compound having the formula IV is directly reacted with the compound having the formula V in the same reaction vessel without further purification.

In some embodiments of the method for synthesizing a substituted or unsubstituted 4-amino-3-benzimidazolyl quinolinone compound and compositions that include such a compound, a compound having the formula VII is reacted with a compound having the formula $HR^7$ or a salt thereof to produce the compound having the formula VIA where the variables $R^5$, $R^6$, and $R^8$ have the values set forth above with respect to the second compound having the formula II and Y is selected from Cl or F.

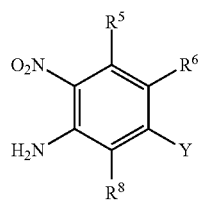

VII

In some such embodiments, the compound having the formula VII is a compound having the formula VIIA or VIIB. In some such embodiments, $R^7$ is a substituted or unsubstituted heterocyclyl group, that, in some embodiments is selected from substituted or unsubstituted piperidinyl groups, piperazinyl groups, or morpholinyl groups. In some such embodiments, $R^7$ is an N-alkyl piperazinyl group such as an N-methyl piperazinyl group such that $HR^7$ has the formula $HR^7(a)$ shown below.

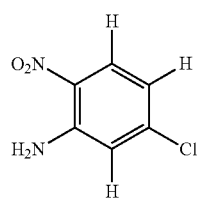

VIIA

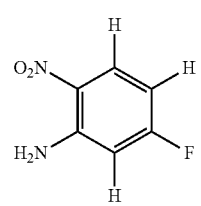

VIIB

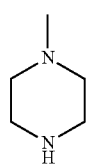

$HR^7(a)$

In some embodiments, the compound having the formula VII is reacted with the compound having the formula $HR^7$, such as N-methylpiperazine at a temperature of from about 70° C. to about 120° C. or of about 80° C. to about 110° C., of from about 85° C. to about 105° C., or of about 100° C. for a period of from about 2 hours to about 24 hours, of from about 4 hours to about 12 hours, or of from about 6 hours to about 10 hours. A variety of suitable solvents such as, but not limited to, water or ethanol may be employed in the reaction of the compound having the formula $HR^7$ with the reaction of the compound having the formula VII. Addition of a solvent such as ethanol to the reaction helps to prevent solidification of the reaction. In some embodiments, any of the reactions of the method are followed by HPLC and are conducted for a period of time until the starting materials are observed to no longer be present in any appreciable amounts.

Improved methods for synthesizing a compound of Formula VIH have been discovered:

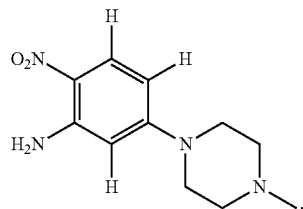

VIH

The methods can be used to synthesize heterocyclic compounds other than VIH. For example, a 5-halo-2-nitroaniline compound such as 5-chloro-2-nitroaniline may be reacted with a N-containing heterocycle such as a substituted or unsubstituted pyrrolidine, a substituted or unsubstituted piperazine such as an N-alkyl piperazine, or a substituted or unsubstituted piperidine to form desired compounds of formula VIHa where Het is a N-containing heterocycle, and a N atom of the heterocycle is bonded to the benzene ring. In some embodiments, the heterocycle is a saturated heterocycle such as a piperazine, piperidine, or pyrrolidine.

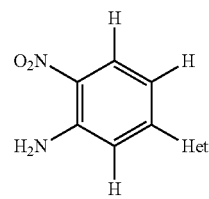

VIHa

In some embodiments, the halo group of the 5-halo-2-nitroaniline compound used in the synthesis is a fluorine or a chlorine such that the compound is 5-fluoro-2-nitroaniline or 5-chloro-2-nitroaniline. Thus, some methods include reacting a mixture of 1-methylpiperazine and a 5-halo-2-nitroaniline compound such as 5-chloro-2-nitroaniline at an internal temperature sufficient to provide a compound of Formula VIH. Excess amounts of the heterocycle may be used to force the reaction to completion.

For example, the methods include reacting a mixture of 1-methylpiperazine and 5-halo-2-nitroaniline in a first solvent and at a first temperature sufficient to provide a compound of Formula VIH in the first solvent, e.g., at from about 70° to about 140° C., at from about 80° to about 120° C., at from about 90° to about 110° C., more typically from about 90° to about 100° C., or even from about 95° to about 100° C. The first solvent is an organic solvent, e.g., an alcohol such as ethanol. The 1-methylpiperazine and 5-halo-2-nitroaniline may be present at a molar ratio ranging from about 0.5:1 to about 10:1. In some embodiments, excess 1-methylpiperazine versus nitroaniline may be used to force the reaction to completion. For example, the 1-methylpiperazine and 5-halo-2-nitroaniline can be present at a molar ratio ranging from about 2:1 to about 5:1, from about 3:1 to about 5:1, or from about 3.5:1 to about 4.5:1. To isolate the compound of Formula VIH from the reaction mixture, a volume of a second solvent, different from the first solvent, is added to the reaction mixture, and forming a slurry of the compound of Formula VIH.

In some embodiments, the second solvent comprises water. In other embodiments, the second solvent consists of or consists essentially of water. In some embodiments, the mixture containing the compound of Formula VIH is cooled to a second temperature not less than 80% of the first temperature (e.g., about 85° to about 95° C.) before the volume of water is added. In still other embodiments, the mixture is cooled to a temperature not less than 90% of the first temperature. Before addition to the mixture, the water is heated to about the same temperature as the mixture, i.e., about the second temperature. The slurry is then formed by cooling the reaction mixture to a third temperature, e.g., about 15° to about 25° C. Over time, the slurry thickens and uniform crystals of VIH are obtained.

In other embodiments, the second solvent is an organic solvent such as heptane. The reaction mixture can be cooled to a second temperature not less than 70% of the initial temperature before adding the second solvent to the mixture (e.g., about 70° C. to about 85° C.). The reaction mixture containing the second solvent is cooled to a third temperature (e.g., about 15° C. to about 25° C.) to form a slurry of the compound of Formula VIH. A second volume of the second solvent may be added during cooling to aid in the formation of crystals of the compound of Formula VIH. As above, the reaction mixture is cooled further to a temperature of, e.g., about 15 to about 25° C., to form crystals of VIH. The crystals of compound VIH may be collected and washed with water by, e.g., filtration. It is advantageous, but not required, that the crystals be substantially free of ethanol before washing with water to avoid production of fine particles that are difficult to handle. After the water wash, the crystals may optionally be washed again with an organic solvent such as heptane and subsequently dried. Drying may be performed in vacuo with or without heating above ambient temperature. The compound of Formula VIH has a purity equal to or greater than 90 percent in some embodiments, equal to or greater than 95 percent in other embodiments, and equal to or greater than 99 percent in yet other embodiments.

In some embodiments, the improved methods for synthesizing a compound of Formula VIH are conducted in a solvent that comprises water in an amount greater than about 50 percent by volume based on the amount of the solvent and/or are reacted in a solvent that comprises an organic solvent component that has a boiling point of greater than about 100° C. at atmospheric pressure. Although compounds of formula VIH may be readily synthesized by reaction of 1-methylpiperazine with 5-halo-2-nitroaniline in ethanol, it has been discovered that reaction times are significantly shortened and excellent yields obtained when these reactions are conducted in water or in a solvent that includes an organic solvent component with a boiling point of about 100° C. Or greater. For example, when the reaction is performed in an aqueous solution with a salt such as NaCl (other salts such as KCl may be used as will be apparent to those skilled in the art) at a concentration ranging from about 0 to about 5 M, the reaction is typically complete (as determined using HPLC) within about 5 to about 6 hours as opposed to 36-40 hours when conducted in ethanol at 97° C. The improved time-efficiency gained by performing the reaction in water or in an aqueous salt solution provides significant cost benefits during manufacturing. When the reaction is conducted in an aqueous NaCl solution at about 100° C. to about 110° C., the product compound was isolated in 94% yield with 99.4% purity by HPLC. This compares favorably with the yield ranging from 90-100 percent when the reaction is performed in ethanol.

In addition to the shortened reaction time, the reaction work up is typically simpler when the formation of VIH is accomplished using the improved methods of the invention. For example, when the synthesis is carried out in an aqueous salt solution at about 100° C. to about 110° C., the workup typically involves adding water to the reaction mixture at about 90° C. to about 105° C., inducing product crystallization. Granular crystals were typically observed at this stage which is desirable as this positively impacts filterability and drying time. After cooling to room temperature (about 20° C. to about 25° C.), the desired product (VIH) may be filtered, washed, and dried in a vacuum oven. Shortened reaction times were also obtained when the reaction of 1-methylpiperazine with 5-chloro-2-nitroaniline was conducted in a solvent that includes an organic solvent component, such as ethylene glycol, that has a boiling point of about 100° C. or greater. When the reaction is conducted in water at about 100° C. to about 108° C., the reaction is typically complete within about 6 to about 7 hours. When the reaction is conducted in ethylene glycol at about 120° C. to about 125° C., the reaction is typically complete within 4-5 hours. In some embodiments the temperature range is from about 95 to about 120° C.

In one aspect, the present invention provides a method of synthesizing a compound of Formula VIH:

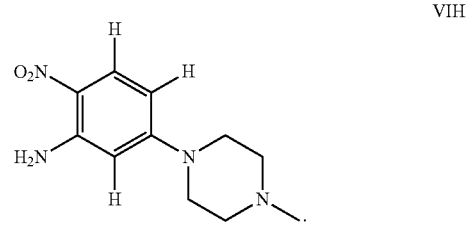

The method includes, in a first reaction mixture, reacting 1-methylpiperazine with 5-halo-2-nitroaniline at an internal temperature sufficient to provide the compound of Formula VIH. In such aspects of the method, the 1-methylpiperazine and the 5-halo-2-nitroaniline are reacted in a solvent that comprises water. In some embodiments, the 5-halo-2-nitroaniline is 5-chloro-2-nitroaniline, and in other embodiments, is 5-fluoro-2-nitroaniline.

In some embodiments, the solvent comprises water in an amount greater than about 50 percent by volume based on the amount of the solvent. In other such embodiments, the solvent comprises water in an amount greater than about 80 percent by volume based on the amount of the solvent. In some such embodiments, the solvent comprises water in an amount greater than about 90 percent by volume based on the amount of the solvent. In still further such embodiments, the solvent comprises water in an amount greater than about 98 percent by volume based on the amount of the solvent. In still further such embodiments, the solvent consists essentially of or consists of water. In still other such embodiments, the solvent consists essentially of or consists of de-ionized or distilled water.

In some embodiments, the solvent is an aqueous solution comprising a salt such as NaCl. In some such embodiments, the concentration of the salt in the aqueous solutions ranges from about 1 to about 5 M. In some such embodiments, the concentration of the salt ranges from about 3 to about 4.5 M an in other embodiments ranges from about 3.5 to about 4.2M.

In some embodiments, the internal temperature is greater than about 95° C. In various such embodiments, the internal temperature ranges from about 99° C. to about 115° C., from about 100° C. to about 110° C., or from about 105° C. to about 110° C. In some embodiments, the reaction is conducted at atmospheric pressure whereas in other embodiments, the reaction is conducted at a pressure up to about 2 atm.

In some embodiments, the 1-methylpiperazine and the 5-halo-2-nitroaniline are reacted at the internal temperature for a reaction time of less than about 20 hours. In some such embodiments, the reaction time is less than about 10 hours. In some such embodiments, the reaction time is less than about 8 hours.

It has been discovered that the use of inorganic bases can reduce the amount of excess 1-methylpiperazine needed to drive the reaction toward product. Use of inorganic bases in some embodied methods results in high yields and high purities of the compound of Formula VIH in less time than the same reaction without the inorganic bases. Thus, in some embodiments, the methods include reacting a mixture of 1-methylpiperazine and 5-halo-2-nitroaniline in a solvent at a temperature sufficient to provide a compound of Formula VIH, the solvent is an aqueous solution comprising a salt and an inorganic base. Suitable inorganic bases for use in the reaction include hydroxides, carbonates and phosphates of alkali and alkali earth metals. Exemplary bases include but are not limited to NaOH, KOH, $Ca(OH)_2$, $Mg(OH)_2$, $Na_2CO_3$, $K_2CO_3$, and $K_3PO_4$.

Methods utilizing such inorganic bases are performed analogously to the above methods utilizing water with salt(s) alone, but with a reduction in the amount of 1-methylpiperazine used to achieve the same yields and product purities. Thus, in some embodiments, the molar ratio of 1-methylpiperazine to 5-halo-2-nitroaniline ranges from about 1.5:1 to about 3:1, or from about 2:1 to about 3:1. In some embodiments, the concentration of salt in the aqueous solution ranges from about 1 to about 5 M, from about 2 to about 5 M in other embodiments, and from about 3 to about 5 M in yet other embodiments.

In other embodiments, methods for synthesizing a compound of Formula VIH include recycling of the mother liquor. These methods include collecting the mother liquor once reaction completion has been determined, adding a base to the mother liquor, recharging the mother liquor with 1-methylpiperazine and 5-halo-2-nitroaniline and re-running the reaction at a temperature sufficient to provide a compound of Formula VIH. This results in a reduction in the overall amount of starting materials, and a reduction in the overall amount of waste liquors generated. The recycling of the mother liquor may be performed one, two, three, four, or more times, or until the yield of product declines. Thus, in some embodiments, methods for synthesizing a heterocyclic compound are provided comprising: reacting 1-methylpiperazine with 5-halo-2-nitroaniline at an internal temperature sufficient to provide a compound of Formula VIH, in a solvent that comprises water, wherein the solvent is an aqueous solution comprising a salt to give a first reaction mixture. In some embodiments, the methods further comprise cooling the first reaction mixture sufficiently to precipitate a first solid comprising the compound of Formula VIH and filtering the first reaction mixture to give a first filtered solid comprising the compound of Formula VIH and a first filtrate comprising the solvent. In other embodiments, the methods further comprise adding to the first filtrate 1-methylpiperazine, 5-halo-2-nitroaniline, and an amount of a base sufficient to neutralize any HCl in the first filtrate, to give a second reaction mixture, at an internal temperature sufficient to provide the compound of Formula VIH. In yet other embodiments, the methods further comprise cooling the second reaction mixture sufficiently to precipitate a second solid comprising the compound of Formula VIH and filtering the second reaction mixture to provide a second filtered solid comprising the compound of Formula VIH and a second filtrate comprising the solvent. In other such embodiments, the methods further comprise adding to the second filtrate, 1-methylpiperazine, 5-halo-2-nitroaniline, and an amount of a base sufficient to neutralize any HCl in the second filtrate, to give a third reaction mixture, at an internal temperature sufficient to provide the compound of Formula VIH. In yet further embodiments, the methods further comprise cooling the third reaction mixture sufficiently to precipitate a third solid comprising the compound of Formula VIH and filtering the third reaction mixture to give a third filtered solid comprising the compound of Formula VIH and a third filtrate comprising the solvent. In some embodiments, the salt is NaCl. In some embodiments, the solvent is a saturated solution of NaCl. In some embodiments, the base is NaOH or KOH. In some embodiments, the internal temperature ranges from about 95° C. to about 120° C. After isolating the compound of Formula VIH at each filtration step, the compound of Formula VIH has a purity equal to or greater than about 90 percent in some embodiments, equal to or greater than about 95 percent in other embodiments, and equal to or greater than 99 percent in yet other embodiments.

In some embodiments, the molar ratio of the 1-methylpiperazine to the 5-halo-2-nitroaniline ranges from about 2:1 to about 10:1 at the start of the reaction, or even from about 0.5:1 to about 10:1 or about 1:1 to about 10:1 at the start of the reaction. In some such embodiments, the molar ratio of the 1-methylpiperazine to the 5-halo-2-nitroaniline ranges from about 3:1 to about 4.5:1 at the start of the reaction. In still other such embodiments, the molar ratio of the 1-methylpiperazine to the 5-halo-2-nitroaniline ranges from about 4:1 to about 4.3:1 at the start of the reaction.

In some embodiments, the yield of the compound of Formula VIH based on the amount of 5-halo-2-nitroaniline is greater than 90 percent. In other embodiments, the yield is greater than 93 percent. In still other embodiments, the yield is greater than 96 percent.

In some embodiments, the method further includes reducing the nitro group of the compound of Formula VIH to an amine to produce a compound of Formula IVA. Some such embodiments further include reacting the compound of Formula IVA with a compound of Formula V or VA to produce a compound of Formula IIC, a compound of Formula IID, or a mixture thereof where $R^{9.4}$ has the values described above. In some embodiments $R^{9.4}$ is an ethyl group. In some embodiments, the compound of Formula IIC, IID, or the mixture thereof is reacted with a compound of Formula IA to provide a compound of Formula IIIB or a tautomer thereof. Some such embodiments further include reacting the compound of Formula IIIB or a tautomer thereof with an acid to provide a salt of the compound of Formula IIIB or the tautomer thereof. In some such embodiments, the acid is lactic acid and the salt is the lactic acid salt of the compound or the tautomer.

In another aspect, the present invention provides a method of synthesizing a compound of Formula VIH:

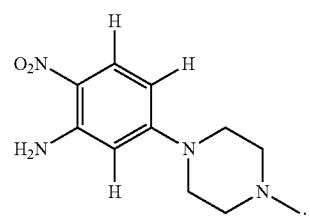

VIH

The method includes reacting 1-methylpiperazine with 5-halo-2-nitroaniline at an internal temperature sufficient to provide the compound of Formula VIH. The 1-methylpiperazine and the 5-halo-2-nitroaniline are reacted in a solvent that comprises an organic solvent component that has a boiling point of greater than 100° C. at atmospheric pressure. In some embodiments, the 5-halo-2-nitroaniline is 5-chloro-2-nitroaniline, and in other embodiments, is 5-fluoro-2-nitroaniline.

In some embodiments, the solvent is a compound of Formula HO—(CH$_2$)$_q$—OH or HO—CH$_2$CH$_2$OCH$_2$CH$_2$—OH, wherein q is selected from 2, 3, or 4. In some such embodiments, the solvent comprises propylene glycol or ethylene glycol. In still further such embodiments, the solvent consists essentially of or consists of propylene glycol or ethylene glycol. In still further such embodiments, the solvent consists essentially of or consists of ethylene glycol.

In some embodiments, the internal temperature is greater than about 95° C. In various such embodiments, the internal temperature ranges from about 99° C. to about 130° C., from about 115° C. to about 130° C., or from about 120° C. to about 125° C. In some embodiments, the reaction is conducted at atmospheric pressure whereas in other embodiments, the reaction is conducted at a pressure up to about 2 atm.

In some embodiments, the 1-methylpiperazine and the 5-halo-2-nitroaniline are reacted at the internal temperature for a reaction time of less than 20 hours. In some such embodiments, the reaction time is less than 10 hours. In some such embodiments, the reaction time is less than 8 hours. In still other embodiments, the reaction time ranges from 3-6 hours, and in some embodiments ranges from 4-5 hours.

In some embodiments, the molar ratio of the 1-methylpiperazine to the 5-halo-2-nitroaniline ranges from about 0.5:1 to about 10:1, about 1:1 to about 10:1, or about 2:1 to about 10:1 at the start of the reaction. In some such embodiments, the molar ratio of the 1-methylpiperazine to the 5-halo-2-nitroaniline ranges from about 3:1 to about 4.5:1 at the start of the reaction. In still other such embodiments, the molar ratio of the 1-methylpiperazine to the 5-halo-2-nitroaniline ranges from about 4:1 to about 4.3:1 at the start of the reaction.

In some embodiments, the yield of the compound of Formula VIH based on the amount of 5-halo-2-nitroaniline is greater than 90 percent. In other embodiments, the yield is greater than 92 percent. In still other embodiments, the yield is greater than 96 percent.

In some embodiments, the method further includes reducing the nitro group of the compound of Formula VIH to an amine to produce a compound of Formula IVA. Some such embodiments further include reacting the compound of Formula IVA with a compound of Formula V or VA to produce a compound of Formula IIC, a compound of Formula IID, or a mixture thereof where R$^{9A}$ has the values described above. In some embodiments R$^{9A}$ is an ethyl group. In some embodiments, the compound of Formula IIC, IID, or the mixture thereof is reacted with a compound of Formula IA to provide a compound of Formula IIIB or a tautomer thereof. Some such embodiments further include reacting the compound of Formula IIIB or a tautomer thereof with an acid to provide a salt of the compound of Formula IIIB or the tautomer thereof. In some such embodiments, the acid is lactic acid and the salt is the lactic acid salt of the compound or the tautomer.

In some embodiments, the substituted or unsubstituted 4-amino-3-benzimidazolyl quinolinone compound is a compound having the formula IIIA, is a tautomer of the compound having the formula IIIA, is a salt of the compound having the formula IIIA, or is a salt of the tautomer of the compound having the formula IIIA and R$^7$ is a substituted or unsubstituted heterocyclyl group

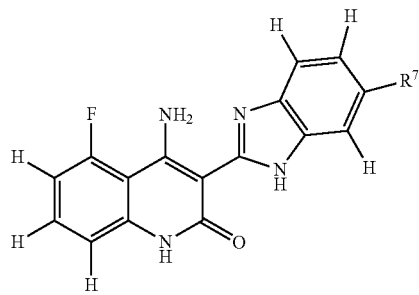

In some such embodiments, R$^7$ is a substituted or unsubstituted heterocyclyl group that is selected from a substituted or unsubstituted piperidinyl group, piperazinyl group, or morpholinyl group. In some embodiments, R$^7$ is a substituted or unsubstituted N-alkyl piperazinyl group such as an N-methyl piperazinyl group, an N-ethyl piperazinyl group, or a N-propyl piperazinyl group.

In some embodiments, the substituted or unsubstituted 4-amino-3-benzimidazolyl quinolinone compound is a compound having the formula IIIB, is a tautomer of the compound having the formula IIIB, is a salt of the compound having the formula IIIB, or is a salt of the tautomer of the compound having the formula IIIB

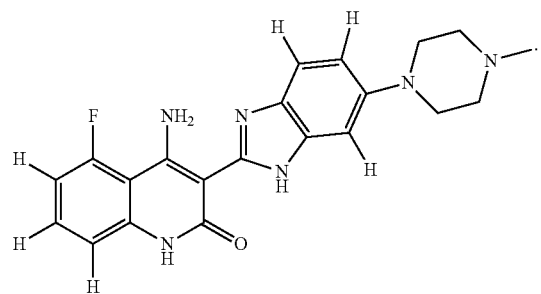

In some embodiments, the method further includes reacting the substituted or unsubstituted 4-amino-3-benzimidazolyl quinolinone compound or a tautomer of the compound with lactic acid, wherein the lactic acid salt of the 4-amino-3-benzimidazolyl quinolinone compound or the tautomer is obtained. In some such embodiments, the compound having the formula IIIB or a tautomer thereof is reacted with lactic acid to produce the lactic acid salt of the compound or tautomer. In some such embodiments, the compound or tautomer is reacted with D,L-lactic acid in water and ethanol and the monolactate salt is produced as a crystalline solid.

The use of a sodium or potassium salt of a base such as, but not limited to, NaHMDS, KHMDS, sodium t-butoxide, or potassium t-butoxide, rather than a lithium salt such as LiHMDS in the reaction of the first compound with the second compound provides a method of producing compositions that include reduced amounts of lithium and in some embodiments may not include any lithium. Furthermore, the use of a base such as potassium t-butoxide results in increased yields of the benzimidazolyl quinolinone compound. Consequently, in some embodiments, the invention provides a composition that includes a benzimidazolyl quinolinone compound having the formula III, a tautomer of the benzimidazolyl quinolinone compound, a salt of the benzimidazolyl quinolinone compound, a salt of the tautomer of the benzimidazolyl compound, or mixtures thereof, wherein the benzimidazolyl quinolinone compound is a compound having the formula III,

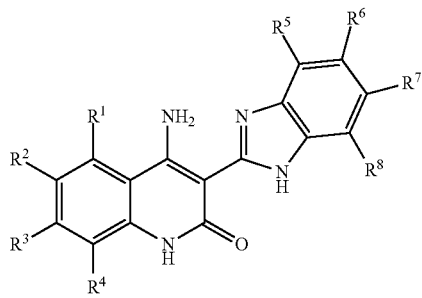

wherein:

$R^1$, $R^2$, $R^3$, and $R^4$ may be the same or different and are independently selected from H, Cl, Br, F, I, —$OR^{16}$ groups, —$NR^{11}R^{12}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, or substituted or unsubstituted heterocyclylalkyl groups;

$R^5$, $R^6$, $R^7$, and $R^8$ may be the same or different and are independently selected from H, Cl, Br, F, I, —$OR^{13}$ groups, —$NR^{14}R^{15}$ groups, —$SR^{16}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted heterocyclylalkyl groups; substituted or unsubstituted alkoxyalkyl groups, substituted or unsubstituted aryloxyalkyl groups, or substituted or unsubstituted heterocyclyloxyalkyl groups;

$R^{10}$ and $R^{13}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, substituted or unsubstituted alkoxyalkyl groups, substituted or unsubstituted aryloxyalkyl groups, or substituted or unsubstituted heterocyclyloxyalkyl groups;

$R^{11}$ and $R^{14}$ may be the same or different and are independently selected from substituted or unsubstituted alkyl groups, substituted or unsubstituted aryl groups, or substituted or unsubstituted heterocyclyl groups;

$R^{12}$ and $R^{15}$ may be the same or different and are independently selected from substituted or unsubstituted alkyl groups, substituted or unsubstituted aryl groups, or substituted or unsubstituted heterocyclyl groups;

$R^{16}$ is selected from substituted or unsubstituted alkyl groups, substituted or unsubstituted aryl groups, or substituted or unsubstituted heterocyclyl groups; and further wherein, the amount of lithium in the composition is less than 1 percent by weight based on the weight of the benzimidazolyl quinolinone compound in the composition.

In some embodiments of the compositions provided herein, the amount of lithium in the composition is less than 0.5 percent, is less than 0.1 percent, is less than 0.05 percent, is less than 0.01 percent, is less than 0.005 percent, or is less than 0.001 by weight based on the weight of the benzimidazolyl quinolinone compound, the tautomer of the benzimidazolyl quinolinone compound, the salt of the benzimidazolyl quinolinone compound, the salt of the tautomer of the benzimidazolyl compound, or the mixtures thereof in the composition. In some such embodiments of the compositions provided herein, lithium is completely absent from the composition. In some embodiments, the composition has less than 1 percent, less than 0.05 percent, or less than 0.01% of the uncyclized intermediate shown in Scheme 1 based on the weight of the benzimidazolyl quinolinone compound.

In some embodiments of the compositions provided herein, the benzimidazolyl quinolinone compound having the formula III is a compound having the formula IIIB

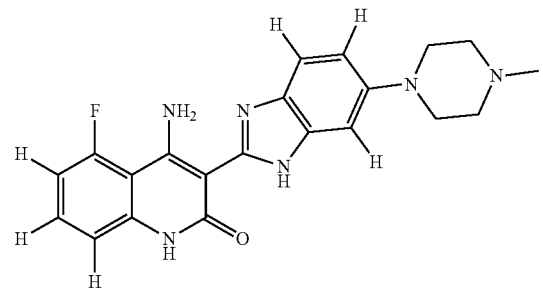

In various groups that include heterocyclyl groups, the heterocyclyl group may be attached in various ways. For example, in an —$OCH_2(CH_2)_q$(heterocyclyl) group, where q is selected from 0, 1, 2, 3, or 4, the heterocyclyl group may be bonded to a methylene carbon of the —$OCH_2(CH_2)_q$ group of the —$OCH_2(CH_2)_q$(heterocyclyl) through various ring members. By way of non-limiting example, where q is 1 and the heterocyclyl group is tetrahydrofuran, the group could be represented by the formula —$OCH_2CH_2$(tetrahydrofuranyl) which corresponds to the following two structures:

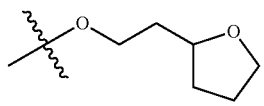

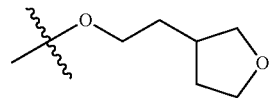

where structure VIII represents the group that can be referred to as the —$OCH_2CH_2$(2-tetrahydrofuranyl) group and structure IX represents the group that can be referred to as the —$OCH_2CH_2$(3-tetrahydrofuranyl) group. When the heterocyclyl group is a N-containing heterocycle, such as, but not limited to piperidine, piperazine, morpholine, or pyrrolidine, the heterocycle can be bonded to the methylene carbon through a ring carbon atom or through a nitrogen atom in the ring of the N-containing heterocycle. Both of these are preferred. Where the heterocyclyl group is a piperidine and q is 2 for an —$OCH_2(CH_2)_q$(heterocyclyl) group, the following structures are possible and preferred:

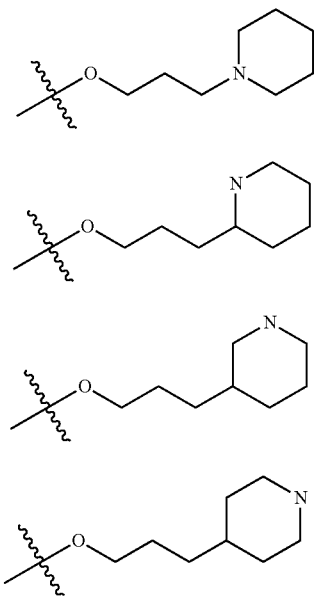

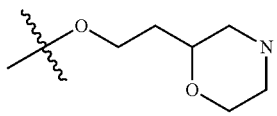

Structure X is an example of a —O(CH$_2$)$_3$(N-piperidinyl) or —O(CH$_2$)$_3$(1-piperidinyl) group. Structure XI is an example of a —O(CH$_2$)-3-(2-piperidinyl) group. Structure XII is an example of a —O(CH$_2$)$_3$(3-piperidinyl) group. Structure XIII is an example of a —O(CH$_2$)$_3$(4-piperidinyl) group. Where the heterocyclyl group is a piperazine and q is 1 for an —OCH$_2$(CH$_2$)$_q$(heterocyclyl) group, the following structures are possible and preferred:

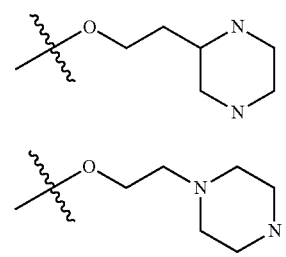

Structure XIV is an example of a —O(CH$_2$)$_2$(2-piperazinyl) group, and structure XV is an example of a —O(CH$_2$)$_2$(1-piperazinyl) or —O(CH$_2$)$_2$(N-piperazinyl) group. Where the heterocyclyl group is a morpholine and q is 1 for an —OCH$_2$(CH$_2$)$_q$(heterocyclyl) group, the following structures are possible and preferred:

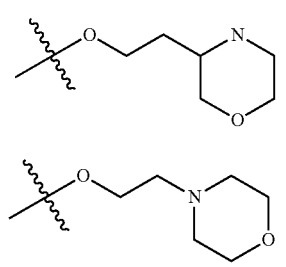

Structure XVI is an example of a —O(CH$_2$)$_2$(3-morpholinyl) group, structure XVII is an example of a —O(CH$_2$)$_2$(4-morpholinyl) or —O(CH$_2$)$_2$(N-morpholinyl) group, and structure XVIII is an example of a —O(CH$_2$)$_2$(2-morpholinyl) group. It will be observed that where the group is a pyrrolidine, and q is 1, the structures available include —O(CH$_2$)$_2$(1-pyrrolidinyl) or —O(CH$_2$)$_2$(N-pyrrolidinyl), —O(CH$_2$)$_2$(2-pyrrolidinyl), and —O(CH$_2$)$_2$(3-pyrrolidinyl).

Scheme 1 depicts one exemplary synthetic route for the synthesis of a compound of a benzimidazolyl quinolinone compound and should not be interpreted to limit the invention in any manner. As shown below, the reaction of a first compound with a second compound is believed to proceed via an uncyclized intermediate. However, this will be understood to not limit the invention in any manner. The potassium salt of the resulting compound having the formula III produced on cyclization of the intermediate has been found to have reduced solubility resulting in precipitation of the product from the reaction. This was surprising and unexpected given that precipitation was not observed when a lithium salt such as LiHMDS was used rather than a potassium salt such as KHMDS. The use of the potassium salt rather than a lithium salt provides a greatly enhanced yield of compounds having the formula III such as compounds having the formula IIIB as shown in Scheme 1 especially when a base such as a potassium alkoxide such as potassium t-butoxide is employed. The reaction of the first compound with the second compound was also found to provide significantly higher yields of compounds having the formula III when the reaction was conducted with solvents and reactants with low water contents. For example, the yield was found to improve significantly when the second compound was dried as described herein such as by azeotropic evaporation from absolute ethanol or in the reaction vessel by repeated addition of THF followed by distillation. The yield of the compound having the formula VI, such as a compound having the formula VIH, produced by the reaction of an N-alkyl piperazine such as N-methyl piperazine with the compound having the formula VII, was increased when the temperature was lowered and the amount of the compound having the formula HR$^7$ was increased with respect to the compound having the formula VI. The temperatures of the reaction were lowered and the reaction was diluted with ethanol during scale up. For example, good yields were obtained when the reaction was conducted at a temperature of 90° C. to 100° C., and the compound having the formula HR$^7$, such as N-methyl piperazine, was present in an amount of greater than 2.5 equivalents with respect to the amount of the compound having the formula VI, such as 5-chloro-2-nitroaniline. In some such embodiments, the compound having the formula HR$^7$ is present in an amount of greater than 2.8, greater than 2.9, greater than 3.0, or from 2.5 to 5 equivalents with respect to the amount of the compound having the formula VI.

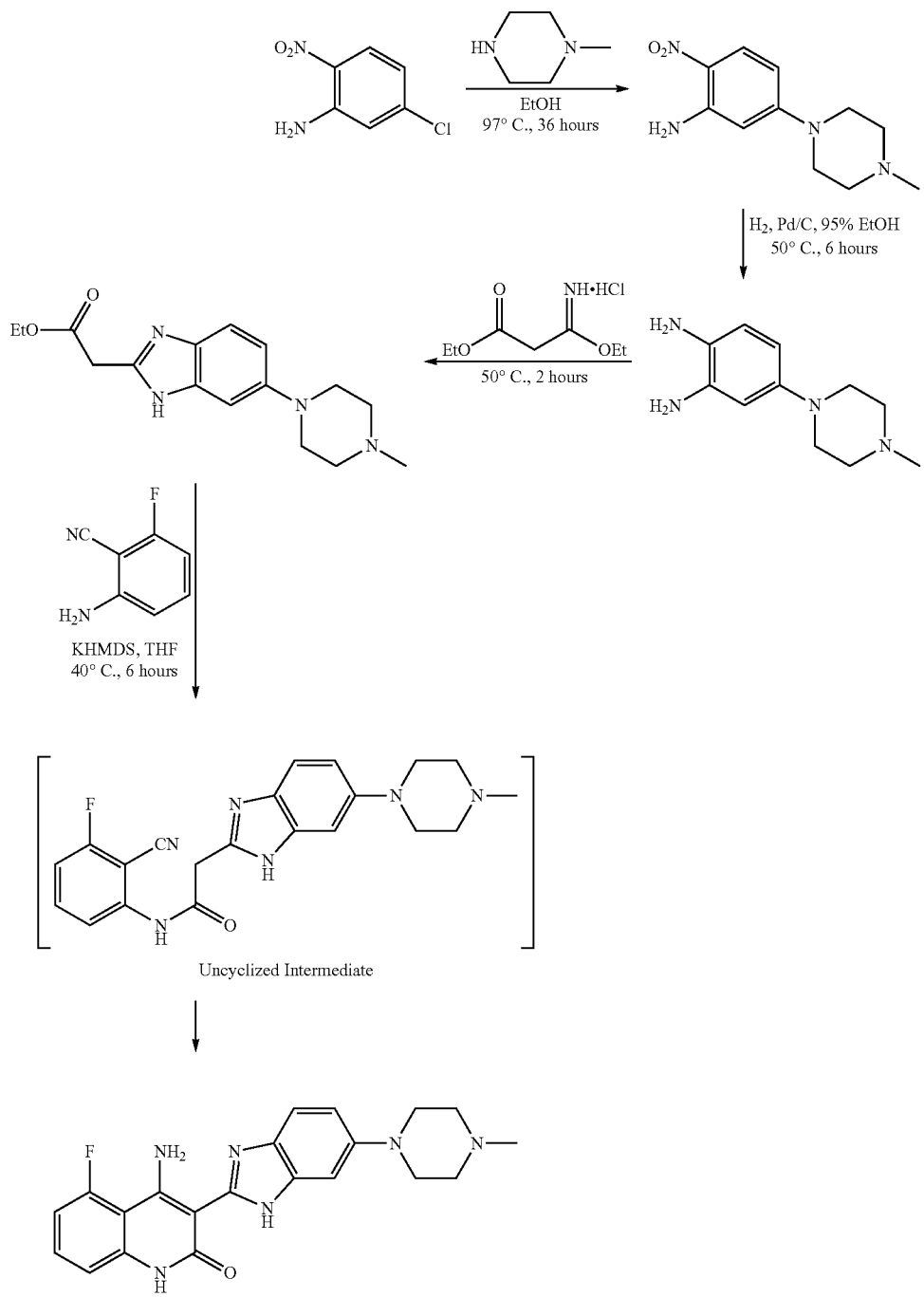

Scheme 2 depicts a method for synthesizing a compound having the formula VA and shows the general application of the method of the invention. Those skilled in the art will understand that the selection of a substituted or unsubstituted diaminobenzene and a substituted or unsubstituted anthranilonitrile allows for the synthesis of a wide variety of compounds having the formula III. Those skilled in the art will also recognize that certain groups may need protection using standard protecting groups for the final cyclization reaction. The extremely versatile synthetic route allows a plethora of compounds having the formula III to be readily prepared by a highly convergent and efficient synthetic route.

Scheme 2

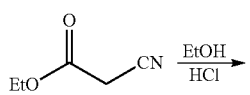

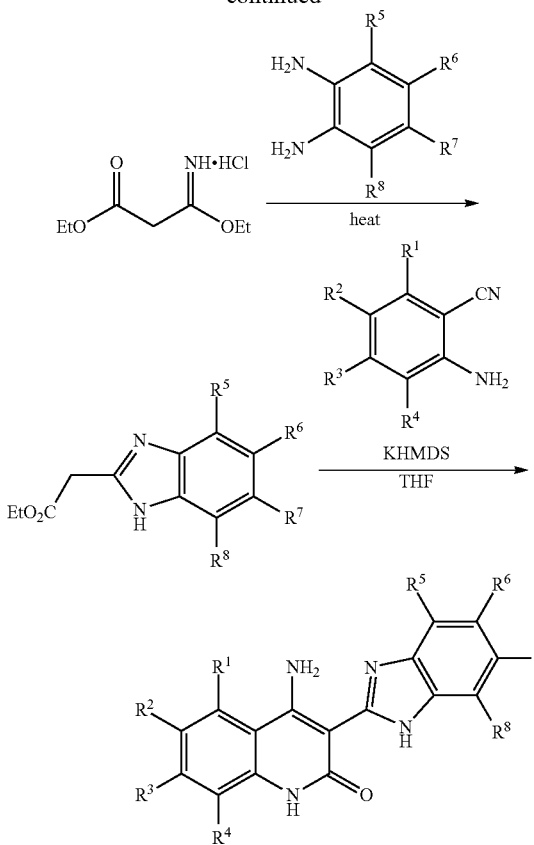

The present invention, thus generally described, will be understood more readily by reference to the following examples, which are provided by way of illustration and are not intended to be limiting of the present invention. The following documents including the examples in the documents are hereby incorporated by reference for all purposes as if fully set forth herein in their entirety: U.S. Pat. No. 6,605,617; U.S. Patent Publication No. 2004/0092535, filed on Aug. 19, 2003; U.S. Provisional Application No. 60/405,729 filed on Aug. 23, 2002; U.S. Provisional Application No. 60/426,107 filed on Nov. 13, 2002; U.S. Provisional Application No. 60/426,226 filed on Nov. 13, 2002; U.S. Provisional Application No. 60/426,282 filed on Nov. 13, 2002; U.S. Provisional Application No. 60/428,210 filed on Nov. 21, 2002; U.S. Provisional Application No. 60/460,327 filed on Apr. 3, 2003; U.S. Provisional Application No 60/681,893 filed on May 17, 2005; U.S. Provisional Application No. 60/460,493 filed on Apr. 3, 2003; U.S. Provisional Application No. 60/478,916 filed on Jun. 16, 2003; U.S. Provisional Application No. 60/484,048 filed on Jul. 1, 2003, and U.S. Provisional Application No. 60/517,915 filed on Nov. 7, 2003.

EXAMPLES

The following abbreviations are used in the Examples:
EtOH: Ethanol
IPA: Isopropanol; 2-propanol
$H_2O$: Water
HCl: Hydrochloric acid
HPLC: High Performance Liquid Chromatography
NMR: Nuclear Magnetic Resonance
KHMDS: Potassium bis(trimethylsilyl)amide
LiHMDS: Lithium bis(trimethylsilyl)amide
NaHMDS: Sodium bis(trimethylsilyl)amide
NaOH: Sodium hydroxide
$N_2$: Nitrogen
TBME: t-Butyl methyl ether
THF: Tetrahydrofuran Nomenclature for the Example compounds was provided using ACD Name version 5.07 software (Nov. 14, 2001) available from Advanced Chemistry Development, Inc., ChemInnovation NamExpert+Nomenclator™ brand software available from ChemInnovation Software, Inc., and AutoNom version 2.2 available in the ChemOffice® Ultra software package version 7.0 available from CambridgeSoft Corporation (Cambridge, Mass.). Some of the compounds and starting materials were named using standard IUPAC nomenclature.

Various starting materials may be obtained from commercial sources and prepared by methods known to one of skill in the art.

Example 1

Synthesis of
5-(4-Methyl-piperazin-1-yl)-2-nitroaniline

Procedure A

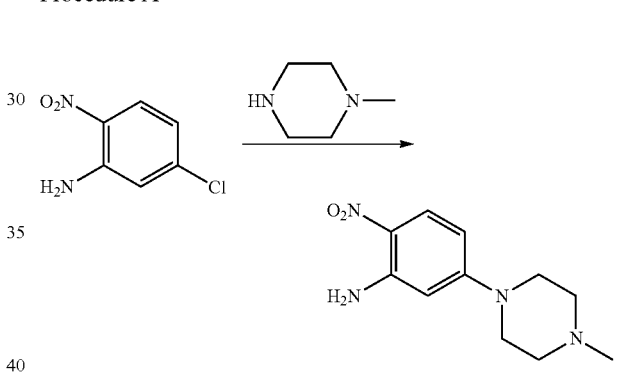

5-Chloro-2-nitroaniline (500 g, 2.898 mol) and 1-methyl piperazine (871 g, 8.693 mol) were placed in a 2000 mL flask fitted with a condenser and purged with $N_2$. The flask was placed in an oil bath at 100° C. and heated until the 5-chloro-2-nitroaniline was completely reacted (typically overnight) as determined by HPLC. After HPLC confirmed the disappearance of the 5-chloro-2-nitroaniline, the reaction mixture was poured directly (still warm) into 2500 mL of room temperature water with mechanical stirring. The resulting mixture was stirred until it reached room temperature and then it was filtered. The yellow solid thus obtained was added to 1000 mL of water and stirred for 30 minutes. The resulting mixture was filtered, and the resulting solid was washed with TBME (500 mL, 2×) and then was dried under vacuum for one hour using a rubber dam. The resulting solid was transferred to a drying tray and dried in a vacuum oven at 50° C. to a constant weight to yield 670 g (97.8%) of the title compound as a yellow powder.

Procedure B

5-Chloro-2-nitroaniline (308.2 g, 1.79 mol) was added to a 4-neck 5000 mL round bottom flask fitted with an overhead stirrer, condenser, gas inlet, addition funnel, and thermometer probe. The flask was then purged with $N_2$. 1-Methylpiperazine (758.1 g, 840 mL, 7.57 mol) and 200 proof ethanol (508 mL) were added to the reaction flask with stirring. The flask was again purged with $N_2$, and the reaction was maintained under N$_2$. The flask was heated in a heating mantle to an internal temperature of 97° C. (+/−5° C.) and maintained at that temperature until the reaction was complete (typically about 40 hours) as determined by HPLC. After the reaction was complete, heating was discontinued and the reaction was cooled to an internal temperature of about 20° C. to 25° C. with stirring, and the reaction was stirred for 2 to 3 hours. Seed crystals (0.20 g, 0.85 mmol) of 5-(4-methyl-piperazin-1-yl)-2-nitroaniline were added to the reaction mixture unless precipitation had already occurred. Water (2,450 mL) was added to the stirred reaction mixture over a period of about one hour while the internal temperature was maintained at a temperature ranging from about 20° C. to 30° C. After the addition of water was complete, the resulting mixture was stirred for about one hour at a temperature of 20° C. to 30° C. The resulting mixture was then filtered, and the flask and filter cake were washed with water (3×2.56 L). The golden yellow solid product was dried to a constant weight of 416 g (98.6% yield) under vacuum at about 50° C. in a vacuum oven.

Procedure C

5-Chloro-2-nitroaniline (401 g, 2.32 mol) was added to a 4-neck 12 L round bottom flask fitted with an overhead stirrer, condenser, gas inlet, addition funnel, and thermometer probe. The flask was then purged with N$_2$. 1-Methylpiperazine (977 g, 1.08 L, 9.75 mol) and 100% ethanol (650 mL) were added to the reaction flask with stirring. The flask was again purged with N$_2$, and the reaction was maintained under N$_2$. The flask was heated in a heating mantle to an internal temperature of 97° C. (+/−5° C.) and maintained at that temperature until the reaction was complete (typically about 40 hours) as determined by HPLC. After the reaction was complete, heating was discontinued and the reaction was cooled to an internal temperature of about 80° C. with stirring, and water (3.15 L) was added to the mixture via an addition funnel over the period of 1 hour while the internal temperature was maintained at 82° C. (+/−3° C.). After water addition was complete, heating was discontinued and the reaction mixture was allowed to cool over a period of no less than 4 hours to an internal temperature of 20-25° C.: The reaction mixture was then stirred for an additional hour at an internal temperature of 20-30° C. The resulting mixture was then filtered, and the flask and filter cake were washed with water (1×1 L), 50% ethanol (1×1 L), and 95% ethanol (1×1 L). The golden yellow solid product was placed in a drying pan and dried to a constant weight of 546 g (99% yield) under vacuum at about 50° C. in a vacuum oven.

Procedure D

5-Chloro-2-nitroaniline (200.0 g, 1.16 mol) was added to a 3-neck 3000 mL round bottom flask fitted with an overhead stirrer, condenser, gas inlet, addition funnel, and thermometer probe. The round bottom flask was then purged with N$_2$. 1-Methylpiperazine (550 g, 552 mL, 4.98 mol) and de-ionized water (330 mL) were added to a 1000 mL Erlenmeyer flask. The aqueous solution of 1-methylpiperazine (~880 mL) was added in a steady stream to the round bottom flask over a period of about 5 minutes. The flask was again purged with N$_2$, and the reaction was maintained under N$_2$. The flask was stirred at about 800 rpm and heated in a heating mantle to an internal temperature of 110° C. (+/−5° C.) and maintained at that temperature until the reaction was complete (typically about 7 hours) as determined by HPLC. De-ionized water (170 mL) and isopropanol (500 mL) were added to an Erlenmeyer flask. The heating of the reaction mixture was discontinued and the aqueous isopropanol mixture was then added to the reaction mixture, in a steady stream. This caused the temperature of the reaction mixture to drop to an internal temperature of about 66.5° C. The mixture crystallized and was held overnight with stirring at a temperature of 40-50° C. The resulting mixture was then filtered, and the flask and filter cake were washed twice with an aqueous isopropanol solution (3:1 water:isopropanol; 2×400 mL) at about 15-20° C. The orange solid product was dried to a constant weight of 267.3 g (97.6% yield) under vacuum at about 50° C. in a vacuum oven.

Procedure E

5-Chloro-2-nitroaniline (150.0 g, 0.87 mol) was added to a 4-neck 3000 mL round bottom flask fitted with an overhead stirrer, condenser, gas inlet, addition funnel, and thermometer probe. The round bottom flask was then purged with N$_2$. Sodium chloride (57.87 g) and de-ionized water (250 mL) were added to a 500 mL Erlenmeyer flask. The resulting 4M sodium chloride solution was added in a steady stream to the round bottom flask. 1-Methylpiperazine (348 g, 386 mL, 3.48 mol) was added to the round bottom flask in a steady stream over a period of about 20 seconds. The flask was again purged with N$_2$, and the reaction was maintained under N$_2$. The flask was heated in a heating mantle to an internal temperature of 110° C. (+/−5° C.) and maintained at that temperature until the reaction was complete (typically about 5-6 hours) as determined by HPLC. De-ionized water (500 mL) was added drop wise to the reaction mixture while maintaining an internal temperature of 108-110 C.°. The resulting slurry was stirred for about 30 minutes. The heating of the reaction mixture was discontinued, an additional 500 mL of water was added to the reaction mixture over a period of about 1 minute, and the reaction mixture was cooled to about 22° C. The resulting mixture was then filtered, and the flask and filter cake were washed with water (750 mL) and with an aqueous ethanol solution (1:1 water:ethanol; 750 mL). The solid product was dried to a constant weight of 192.8 g (93.9% yield) under vacuum at about 50° C. in a vacuum oven.

Procedure F

5-Chloro-2-nitroaniline (100.0 g, 0.58 mol) was added to a 3-neck 2000 mL round bottom flask fitted with an overhead stirrer, condenser, gas inlet, addition funnel, and thermometer probe. The round bottom flask was then purged with N$_2$. Ethylene glycol (100 mL) was added to the round bottom flask and the mixture was stirred under N$_2$. 1-Methylpiperazine (232 g, 257 mL, 2.32 mol) was then added to the round bottom flask. The flask was again purged with N$_2$, and the reaction was maintained under N$_2$. The flask was heated in a heating mantle to an internal temperature of 122° C. (+/−5° C.) and maintained at that temperature until the reaction was complete (typically about 4-5 hours) as determined by HPLC. The heating of the reaction mixture was discontinued and water (800 mL) was added to the reaction mixture over a period of about 6 minutes. The resulting slurry was heated to an internal temperature of about 103° C. and stirred for about 30 minutes. The slurry was then cooled to an internal temperature of 20-25° C. with stirring overnight (~14 hours). The resulting mixture was then filtered, and the flask and filter cake were washed twice with water (2×500 mL) and once with an aqueous ethanol solution (1:1 water:ethanol; 500 mL). The resulting solid product was dried to a constant weight of 126.9 g (92.7% yield) under vacuum at about 50° C. in a vacuum oven.

Procedure G

A 1-L, 4-neck round bottom flask was equipped with a heating mantle, an overhead stirrer, condenser, nitrogen inlet, and thermocouple. The flask was charged with 5-chloro-2-nitroaniline (150 g, 869 mmol, 1 equiv), 1-methylpiperazine (348 mL, 386 g, 3.48 mol, 4 equiv) and 4M aqueous NaCl (247 mL). The contents of the flask were stirred and purged with N$_2$ for at least 15 min. The reactor was then heated until an internal temperature of 110-112° C. was reached. The contents were stirred for 7-8 h until the reaction was complete as determined by HPLC. After completion, the reaction mixture was cooled to 20° C. over 2 h to precipitate the product as a slurry, and stirring was continued for an additional 16 h. The solid was vacuum filtered, and the mother liquor collected in the original reaction vessel. The solids were washed on the filter with $H_2O$ (2×250 mL), followed by soaking in heptane (200 mL) for 0.5 h. The slurry was again filtered via vacuum, and dried in vacuo (50° C., 30 in. Hg) to yield 5-(4-methyl-piperazin-1-yl)-2-nitroaniline (197.8 g, 96.3% yield). Residual N-methylpiperazine was not detected by $^1H$ NMR.

The mother liquor of the reaction was recycled by the addition of NaOH pellets (34.9 g, 869 mmol, 1 equiv) to the mother liquor, followed by stirring until the NaOH was dissolved. 1-Methylpiperazine (96.5 mL, 869 mmol, 1 equiv) and 5-chloro-2-nitroaniline (150 g, 869 mmol) were charged to the vessel. Purging, followed by heating to completion, cooling, filtration, and washing with heptane was repeated as above to yield 5-(4-methyl-piperazin-1-yl)-2-nitroaniline (203.2 g, 98.9% yield). Residual N-methylpiperazine was not detected by $^1H$ NMR.

The mother liquor was recycled a second time according to the above procedure to yield 5-(4-methyl-piperazin-1-yl)-2-nitroaniline (203.43 g, 99.0% yield). Less than 1% residual N-methylpiperazine was detected by $^1H$ NMR.

Procedure H

A 4-neck, 5-L round bottom flask in a heating mantle was equipped with an overhead stirrer, condenser, $N_2$ inlet, and thermocouple. 5-Chloro-2-nitroaniline (365.3 g, 2.11 mol) and 1-methylpiperazine (848.6 g, 8.46 mol, 4 equiv) were charged to the flask along with 200-proof EtOH (595 mL). This mixture was stirred and purged with $N_2$ for not less than 15 min. The reaction mixture was then heated, with stirring, until an internal temperature of 97° C.±5° C. was reached. Stirring was continued while maintaining a temperature of 97° C.±5° C. until the reaction was complete (ca. 41 h), as determined by HPLC. De-ionized $H_2O$ (1900 mL) was pre-heated to ca. 90° C. in a separate vessel. The reaction mixture was cooled to 90° C. and the pre-heated $H_2O$ (1900 mL) was transferred to the reaction vessel over 2-3 min. The entire the reaction mixture was then cooled to 25° C. over 4 h. When the temperature reached about 80° C., the product precipitated as a thin slurry that continued to thicken as the suspension cooled. The crude product was then collected by vacuum filtration on a Buchner funnel. The mother liquor was recycled though the reaction Vessel to transfer residual solids to the filter. The crude product was washed with fresh de-ionized $H_2O$ (2×900 mL). The product was dried in vacuo (80° C., 28-30 in. Hg) until constant weight was reached (ca. 21 h). The product was collected in 94.1% yield (471 g). Residual N-methylpiperazine was not detected by $^1H$ NMR.

Procedure I

A 4-neck, 5-L round bottom flask in a heating mantle was equipped with an overhead stirrer, condenser, combination gas inlet/thermocouple (via a Claissen adapter), and addition funnel. 5-chloro-2-nitroaniline (500 g, 2.90 mol) was charged to the reactor and purged with $N_2$, followed by the addition of 1-methylpiperazine (1160 g, 1.28 L, 11.58 mol) and 200 proof EtOH (811 mL) to the reactor. The mixture was stirred and the $N_2$ purge continued for not less than 15 min. The reaction mixture was heated to 97° C.±5° C. The stirring was continued and the temperature held at 97° C.±5° C. until the reaction was complete by HPLC (ca. 40 h).

The reaction mixture was then cooled to 75-80° C. and heptane (375 mL) was added over 5-10 min. Following heptane addition, the reaction mixture was cooled to 65° C.±3° C. to precipitate the product. (If precipitation has not occurred, the solution may be seeded with 5-(4-methyl-piperazin-1-yl)-2-nitroaniline and held for 20-30 min. Additional heptane (125 mL) may be added to aid in precipitation). After cooling the reaction mixture to 65° C., additional heptane (1.63 L) was added to the slurry, over 30-45 min while maintaining the temperature at 65° C.±3° C. After heptane addition, the slurry was cooled to 17-22° C. over 1 h and held at that temperature for not less than 1 h. The product was filtered on a 3 L, coarse-fritted, vacuum funnel. The mother liquor was recycled though the reaction vessel to transfer residual solids: De-ionized $H_2O$ (2.00 L) was added to the funnel and held in the funnel for not less than 5 minutes. The water was then removed by vacuum filtration. The solid was washed with fresh de-ionized $H_2O$ (2×1.1 L) on the filter. Heptane (1.5 L) was added to the funnel and allowed to penetrate the cake for not less than 30 min, after which time the vacuum was applied to remove the heptane. The product was dried in vacuo (75-80° C., 28-30 in. Hg) until constant weight was reached. 5-(4-methyl-piperazin-1-yl)-2-nitroaniline was obtained in 92.9% yield (636 g). Residual N-methylpiperazine was not detected by $^1H$ NMR.

Procedure J

To a 4-dram vial was added 5-Chloro-2-nitroaniline (0.5 g, 2.90 mmol, 1 equiv.), NaOH (0.229 g, 5.71 mmol, 1.98 equiv.), 4'M NaCl (0.82 mL, aq.), and 1-methylpiperazine (0.643 g, 0.71 mL, 5.79 mmol, 2 equiv.). The mixture was heated on a hot plate to 105° C. for 22 h. De-ionized $H_2O$ (6 mL) was added to the mixture, which was cooled to room temperature, and the precipitate collected on a Buchner funnel. The precipitate was then washed with de-ionized $H_2O$ (5 mL) and heptane (5 mL). After drying in a vacuum oven (80° C., 30 in. Hg) overnight, the product (0.624 g, 91.1%) was collected. According to HPLC analysis, the sample had a purity of 99.6%.

5-(4-Methyl-piperazin-1-yl)-2-nitroaniline $^1H$ NMR (400 MHz DMSO-d6) δ: 7.80 ppm (d, J=7.7 Hz, 1H), 7.25 ppm (s, 2H), 6.38 ppm (dd, J=5.0 Hz, J=5.0 Hz, 4H), 2.39 ppm (dd, J=5.0 Hz, J=5.0 Hz, 4H), 2.20 ppm (s, 3H).

Example 2

Synthesis of [6-(4-Methyl-piperazin-1-yl)-1H-benzimidazol-2-yl]-acetic acid ethyl ester

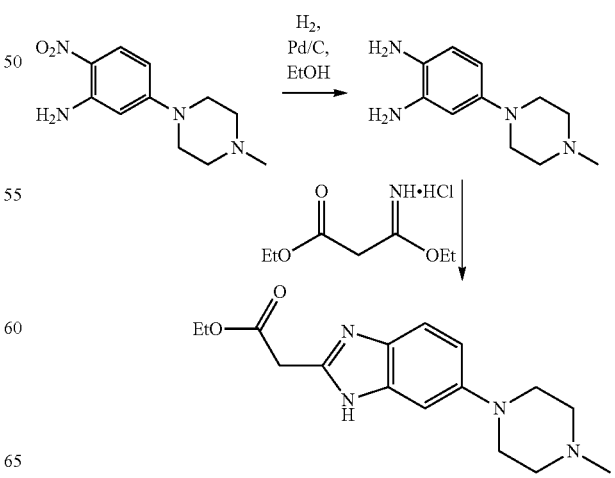

Procedure A

A 5000 mL, 4-neck flask was fitted with a stirrer, thermometer, condenser, and gas inlet/outlet. The equipped flask was charged with 265.7 g (1.1.2 mol. 1.0 eq) of 5-(4-methyl-piperazin-1-yl)-2-nitroaniline and 2125 mL of 200 proof EtOH. The resulting solution was purged with $N_2$ for 15 minutes. Next, 20.0 g of 5% Pd/C (50% $H_2O$ w/w) was added. The reaction was vigorously stirred at 40-50° C. (internal temperature) while $H_2$ was bubbled through the mixture. The reaction was monitored hourly for the disappearance of 5-(4-methyl-piperazin-1-yl)-2-nitroaniline by HPLC. The typical reaction time was 6 hours.

After all the 5-(4-methyl-piperazin-1-yl)-2-nitroaniline had disappeared from the reaction, the solution was purged with $N_2$ for 15 minutes. Next, 440.0 g (2.25 mol) of ethyl 3-ethoxy-3-iminopropanoate hydrochloride was added as a solid. The reaction was stirred at 40-50° C. (internal temperature) until the reaction was complete. The reaction was monitored by following the disappearance of the diamino compound by HPLC. The typical reaction time was 1-2 hours. After the reaction was complete, it was cooled to room temperature and filtered through a pad of Celite filtering material. The Celite filtering material was washed with absolute EtOH (2×250 mL), and the filtrate was concentrated under reduced pressure providing a thick brown/orange oil. The resulting oil was taken up in 850, mL of a 0.37% HCl solution. Solid NaOH (25 g) was then added in one portion, and a precipitate formed. The resulting mixture was stirred for 1 hour and then filtered. The solid was washed with $H_2O$ (2×400 mL) and dried at 50° C. in a vacuum oven providing 251.7 g (74.1%) of [6-(4-methyl-piperazin-1-yl)-1H-benzoimidazol-2-yl]-acetic acid ethyl ester as a pale yellow powder.

Procedure B

A 5000 mL, 4-neck jacketed flask was fitted with a mechanical stirrer, condenser, temperature probe, gas inlet, and oil bubbler. The equipped flask was charged with 300 g (1.27 mol) of 5-(4-methyl-piperazin-1-yl)-2-nitroaniline and 2400 mL of 200 proof EtOH (the reaction may be and has been conducted with 95% ethanol and it is not necessary to use 200 proof ethanol for this reaction). The resulting solution was stirred and purged with $N_2$ for 15 minutes. Next, 22.7 g of 5% Pd/C (50% $H_2O$ w/w) was added to the reaction flask. The reaction vessel was purged with $N_2$ for 15 minutes. After purging with $N_2$, the reaction vessel was purged with $H_2$ by maintaining a slow, but constant flow of $H_2$ through the flask. The reaction was stirred at 45-55° C. (internal temperature) while $H_2$ was bubbled through the mixture until the 5-(4-methyl-piperazin-1-yl)-2-nitroaniline was completely consumed as determined by HPLC. The typical reaction time was 6 hours.

After all the 5-(4-methyl-piperazin-1-yl)-2-nitroaniline had disappeared from the reaction, the solution was purged with $N_2$ for 15 minutes. The diamine intermediate is air sensitive so care was taken to avoid exposure to air. 500 g (2.56 mol) of ethyl 3-ethoxy-3-iminopropanoate hydrochloride was added to the reaction mixture over a period of about 30 minutes. The reaction was stirred at 45-55° C. (internal temperature) under $N_2$ until the diamine was completely consumed as determined by HPLC. The typical reaction time was about 2 hours. After the reaction was complete, the reaction was filtered while warm through a pad of Celite. The reaction flask and Celite were then washed with 200 proof EtOH (3×285 mL). The filtrates were combined in a 5000 mL flask, and about 3300 mL of ethanol was removed under vacuum producing an orange oil. Water (530 mL) and then 1M HCL (350 mL) were added to the resulting oil, and the resulting mixture was stirred. The resulting solution was vigorously stirred while 30% NaOH (200 mL) was added over a period of about 20 minutes maintaining the internal temperature at about 25-30° C. while the pH was brought to between 9 and 10. The resulting suspension was stirred for about 4 hours while maintaining the internal temperature at about 20-25° C. The resulting mixture was filtered, and the filter cake was washed with $H_2O$ (3×300 mL). The collected solid was dried to a constant weight at 50° C. under vacuum in a vacuum oven providing 345.9 g (90.1%) of [6-(4-methyl-piperazin-1-yl)-1H-benzoimidazol-2-yl]-acetic acid ethyl ester as a pale yellow powder. In an alternative work up procedure, the filtrates were combined and the ethanol was removed under vacuum until at least about 90% had been removed. Water at a neutral pH was then added to the resulting oil, and the solution was cooled to about 0° C. An aqueous 20% NaOH solution was then added slowly with rapid stirring to bring the pH up to 9.2 (read with pH meter). The resulting mixture was then filtered and dried as described above. The alternative work up procedure provided the light tan to light yellow product in yields as high as 97%.

Example 3

Method for Reducing Water Content of [6-(4-Methyl-piperazin-1-yl)-1H-benzoimidazol-2-yl]-acetic acid ethyl ester

[6-(4-Methyl-piperazin-1-yl)-1H-benzimidazol-2-yl]-acetic acid ethyl ester (120.7 grams) that had been previously worked up and dried to a water content of about 8-9% $H_2O$ was placed in a 2000 mL round bottom flask and dissolved in absolute ethanol (500 mL). The amber solution was concentrated to a thick oil using a rotary evaporator with heating until all solvent was removed. The procedure was repeated two more times. The thick oil thus obtained was left in the flask and placed in a vacuum oven heated at 50° C. overnight. Karl Fisher analysis results indicated a water content of 5.25%. The lowered water content obtained by this method provided increased yields in the procedure of Example 4. Other solvents such as toluene and THF may be used in place of the ethanol for this drying process.

Example 4

Synthesis of 4-Amino-5-fluoro-3-[6-(4-methyl-piperazin-1-yl)-1H-benzimidazol-2-yl]-1H-quinolin-2-one Procedure A

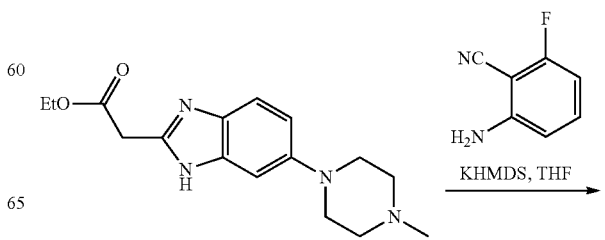

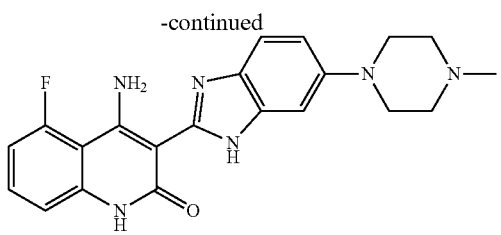

[6-(4-Methyl-piperazin-1-yl)-1H-benzimidazol-2-yl]-acetic acid ethyl ester (250 g, 820 mmol) (dried with ethanol as described above) was dissolved in THF (3800 mL) in a 5000 mL flask fitted with a condenser, mechanical stirrer, temperature probe, and purged with argon. 2-Amino-6-fluoro-benzonitrile (95.3 g, 700 mmol) was added to the solution, and the internal temperature was raised to 40° C. When all the solids had dissolved and the solution temperature had reached 40° C., solid KHMDS (376.2 g, 1890 mmol) was added over a period of 5 minutes. When addition of the potassium base was complete, a heterogeneous yellow solution was obtained, and the internal temperature had risen to 62° C. After a period of 60 minutes, the internal temperature decreased back to 40° C., and the reaction was determined to be complete by HPLC (no starting material or uncyclized intermediate was present). The thick reaction mixture was then quenched by pouring it into $H_2O$ (6000 mL) and stirring the resulting mixture until it had reached room temperature. The mixture was then filtered, and the filter pad was washed with water (1000 mL 2×). The bright yellow solid was placed in a drying tray and dried in a vacuum oven at 50° C. overnight providing 155.3 g (47.9%) of the desired 4-amino-5-fluoro-3-[6-(4-methyl-piperazin-1-yl)-1H-benzimidazol-2-yl]-1H-quinolin-2-one.

Procedure B

A 5000 mL 4-neck jacketed flask was equipped with a distillation apparatus, a temperature probe, a $N_2$ gas inlet, an addition funnel, and a mechanical stirrer. [6-(4-Methyl-piperazin-1-yl)-1H-benzimidazol-2-yl]-acetic acid ethyl ester (173.0 g, 570 mmol) was charged into the reactor, and the reactor was purged with $N_2$ for 15 minutes. Dry THF (2600 mL) was then charged into the flask with stirring. After all the solid had dissolved, solvent was removed by distillation (vacuum or atmospheric (the higher temperature helps to remove the water) using heat as necessary. After 1000 mL of solvent had been removed, distillation was stopped and the reaction was purged with $N_2$. 1000 mL of dry THF was then added to the reaction vessel, and when all solid was dissolved, distillation (vacuum or atmospheric) was again conducted until another 1000 mL of solvent had been removed. This process of adding dry THF and solvent removal was repeated at least 4 times (on the 4$^{th}$ distillation, 60% of the solvent is removed instead of just 40% as in the first 3 distillations) after which a 1 mL sample was removed for Karl Fischer analysis to determine water content. If the analysis showed that the sample contained less than 0.20% water, then reaction was continued as described in the next paragraph. However, if the analysis showed more than 0.20% water, then the drying process described above was continued until a water content of less than 0.20% was achieved.

After a water content of less than or about 0.20% was achieved using the procedure described in the previous paragraph, the distillation apparatus was replaced with a reflux condenser, and the reaction was charged with 2-amino-6-fluoro-benzonitrile (66.2 g, 470 mmol)(in some procedures 0.95 equivalents is used). The reaction was then heated to an internal temperature of 38-42° C. When the internal temperature had reached 38-42° C., KHMDS solution (1313 g, 1.32 mol, 20% KHMDS in THF) was added to the reaction via the addition funnel over a period of 5 minutes maintaining the internal temperature at about 38-50° C. during the addition. When addition of the potassium base was complete, the reaction was stirred for 3.5 to 4.5 hours (in some examples it was stirred for 30 to 60 minutes and the reaction may be complete within that time) while maintaining the internal temperature at from 38-42° C. A sample of the reaction was then removed and analyzed by HPLC. If the reaction was not complete, additional KHMDS solution was added to the flask over a period of 5 minutes and the reaction was stirred at 38-42° C. for 45-60 minutes (the amount of KHMDS solution added was determined by the following: If the IPC ratio is <3.50, then 125 mL was added; if $10.0 \geq$ IPC ratio then 56 mL was added; if $20.0 \geq$ IPC ratio $\geq 10$, then 30 mL was added. The IPC ratio is equal to the area corresponding to 4-amino-5-fluoro-3-[6-(4-methyl-piperazin-1-yl)-1H-benzimidazol-2-yl]-1H-quinolin-2-one) divided by the area corresponding to the uncyclized intermediate). Once the reaction was complete (IPC ratio>20), the reactor was cooled to an internal temperature of 25-30° C., and water (350 mL) was charged into the reactor over a period of 15 minutes while maintaining the internal temperature at 25-35° C. (in one alternative, the reaction is conducted at 40° C. and water is added within 5 minutes. The quicker quench reduces the amount of impurity that forms over time). The reflux condenser was then replaced with a distillation apparatus and solvent was removed by distillation (vacuum or atmospheric) using heat as required. After 1500 mL of solvent had been removed, distillation was discontinued and the reaction was purged with $N_2$. Water (1660 mL) was then added to the reaction flask while maintaining the internal temperature at 20-30° C. The reaction mixture was then stirred at 20-30° C. for 30 minutes before cooling it to an internal temperature of 5-10° C. and then stirring for 1 hour. The resulting suspension was filtered, and the flask and filter cake were washed with water (3×650 mL). The solid thus obtained was dried to a constant weight under vacuum at 50° C. in a vacuum oven to provide 103.9 g (42.6% yield) of 4-amino-5-fluoro-3-[6-(4-methyl-piperazin-1-yl)-1H-benzimidazol-2-yl]-1H-quinolin-2-one as a yellow powder.

Procedure C

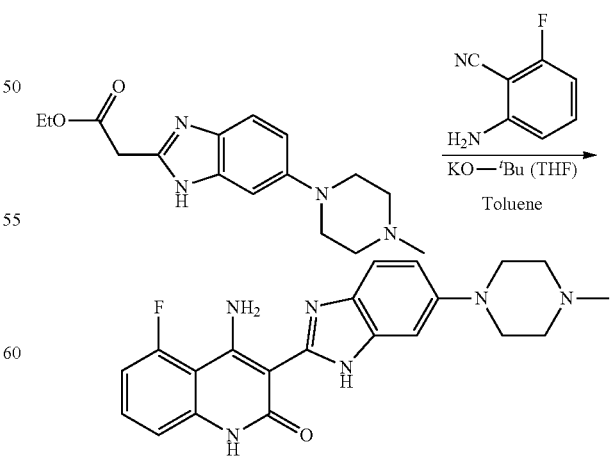

[6-(4-Methyl-piperazin-1-yl)-1H-benzimidazol-2-yl]-acetic acid ethyl ester (608 g, 2.01 mol) (dried) and 2-amino- 6-fluoro-benzonitrile (274 g, 2.01 mol) were charged into a 4-neck 12 L flask seated on a heating mantle and fitted with a condenser, mechanical stirrer, gas inlet, and temperature probe. The reaction vessel was purged with $N_2$, and toluene (7.7 L) was charged into the reaction mixture while it was stirred. The reaction vessel was again purged with $N_2$ and maintained under $N_2$. The internal temperature of the mixture was raised until a temperature of 63° C. (+/−3° C.) was achieved. The internal temperature of the mixture was maintained at 63° C. (+1-3° C.) while approximately 2.6 L of toluene was distilled from the flask under reduced pressure (380+/−10 torr, distilling head t=40° C. (+/−10° C.) (Karl Fischer analysis was used to check the water content in the mixture. If the water content was greater than 0.03%, then another 2.6 L of toluene was added and distillation was repeated. This process was repeated until a water content of less than 0.03% was achieved). After a water content of less than 0.03% was reached, heating was discontinued, and the reaction was cooled under $N_2$ to an internal temperature of 17-19° C. Potassium t-butoxide in THF (20% in THF; 3.39 kg, 6.04 moles potassium t-butoxide) was then added to the reaction under $N_2$ at a rate such that the internal temperature of the reaction was kept below 20° C. After addition of the potassium t-butoxide was complete, the reaction was stirred at an internal temperature of less than 20° C. for 30 minutes. The temperature was then raised to 25° C., and the reaction was stirred for at least 1 hour. The temperature was then raised to 30° C., and the reaction was stirred for at least 30 minutes. The reaction was then monitored for completion using HPLC to check for consumption of the starting materials (typically in 2-3 hours, both starting materials were consumed (less than 0.5% by area % HPLC)). If the reaction was not complete after 2 hours, another 0.05 equivalents of potassium t-butoxide was added at a time, and the process was completed until HPLC showed that the reaction was complete. After the reaction was complete, 650 mL of water was added to the stirred reaction mixture. The reaction was then warmed to an internal temperature of 50° C. and the THF was distilled away (about 3 L by volume) under reduced pressure from the reaction mixture. Water (2.6 L) was then added drop wise to the reaction mixture using an addition funnel. The mixture was then cooled to room temperature and stirred for at least 1 hour. The mixture was then filtered, and the filter cake was washed with water (1.2 L), with 70% ethanol (1.2 L), and with 95% ethanol (1.2 L). The bright yellow solid was placed in a drying tray and dried in a vacuum oven at 50° C. until a constant weight was obtained providing 674 g (85.4%) of the desired 4-amino-5-fluoro-3-[6-(4-methyl-piperazin-1-yl)-1H-benzimidazol-2-yl]-1H-quinolin-2-one.

Example 5

Purification of 4-Amino-5-fluoro-3-[6-(4-methyl-piperazin-1-yl)-1H-benzimidazol-2-yl]-1H-quinolin-2-one A 3000 mL 4-neck flask equipped with a condenser, temperature probe, $N_2$ gas inlet, and mechanical stirrer was placed in a heating mantle. The flask was then charged with 4-amino-5-fluoro-3-[6-(4-methyl-piperazin-1-yl)-1H-benzimidazol-2-yl]-1H-quinolin-2-one (101.0 g, 0.26 mol), and the yellow solid was suspended in 95% ethanol (1000 mL) and stirred. In some cases an 8:1 solvent ratio is used. The suspension was then heated to a gentle reflux (temperature of about 76° C.) with stirring over a period of about 1 hour. The reaction was then stirred for 45-75 minutes while refluxed. At this point, the heat was removed from the flask and the suspension was allowed to cool to a temperature of 25-30° C. The suspension was then filtered, and the filter pad was washed with water (2×500 mL). The yellow solid was then placed in a drying tray and dried in a vacuum oven at 50° C. until a constant weight was obtained (typically 16 hours) to obtain 97.2 g (96.2%) of the purified product as a yellow powder.

Example 6

Preparation of Lactic Acid salt of 4-Amino-5-fluoro-3-[6-(4-methyl-piperazin-1-yl)-1H-benzimidazol-2-yl]-1H-quinolin-2-one

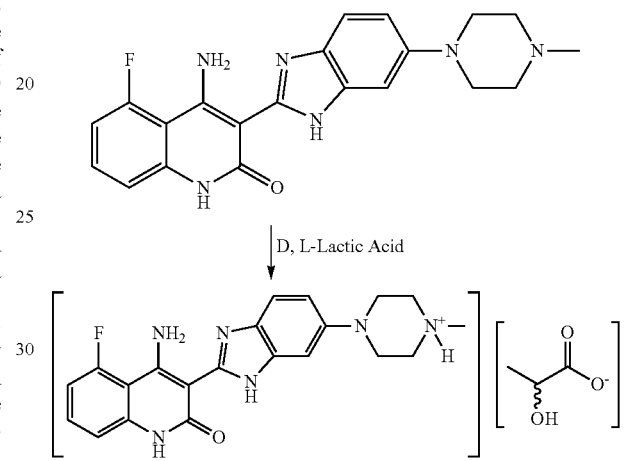

A 3000 mL 4-necked jacketed flask was fitted with a condenser, a temperature probe, a $N_2$ gas inlet, and a mechanical stirrer. The reaction vessel was purged with $N_2$ for at least 1,5 minutes and then charged with 4-amino-5-fluoro-3-[6-(4-methyl-piperazin-1-yl)-1H-benzimidazol-2-yl]-1H-quinolin-2-one (484 g, 1.23 mol). A solution of D,L-Lactic acid (243.3 g, 1.72 mol of monomer—see the following paragraph), water (339 mL), and ethanol (1211 mL) was prepared and then charged to the reaction flask. Stirring was initiated at a medium rate, and the reaction was heated to an internal temperature of 68-72° C. The internal temperature of the reaction was maintained at 68-72° C. for 15-45 minutes and then heating was discontinued. The resulting mixture was filtered through a 10-20 micron frit collecting the filtrate in a 12 L flask. The 12 L flask was equipped with an internal temperature probe, a reflux condenser, an addition funnel, a gas inlet an outlet, and an overhead stirrer. The filtrate was then stirred at a medium rate and heated to reflux (internal temperature of about 78° C.). While maintaining a gentle reflux, ethanol (3,596 mL) was charged to the flask over a period of about 20 minutes. The reaction flask was then cooled to an internal temperature ranging from about 64-70° C. within 15-25 minutes and this temperature was maintained for a period of about 30 minutes. The reactor was inspected for crystals. If no crystals were present, then crystals of the lactic acid salt of 4-amino-5-fluoro-3-[6-(4-methyl-piperazin-1-yl)-1H-benzimidazol-2-yl]-1H-quinolin-2-one (484 mg, 0.1 mole %) were added to the flask, and the reaction was stirred at 64-70° C. for 30 minutes before again inspecting the flask for crystals.

Once crystals were present, stirring was reduced to a low rate and the reaction was stirred at 64-70° C. for an additional 90 minutes. The reaction was then cooled to about 0° C. over a period of about 2 hours, and the resulting mixture was filtered through a 25-50 micron fritted filter. The reactor was washed with ethanol (484 mL) and stirred until the internal temperature was about 0° C. The cold ethanol was used to wash the filter cake, and this procedure was repeated 2 more times. The collected solid was dried to a constant weight at 50° C. under vacuum in a vacuum oven yielding 510.7 g (85.7%) of the crystalline yellow lactic acid salt of 4-amino-5-fluoro-3-[6-(4-methyl-piperazin-1-yl)-1H-benzimidazol-2-yl]-1H-quinolin-2-one. A rubber dam or inert conditions were typically used during the filtration process. While the dry solid did not appear to be very hygroscopic, the wet filter cake tends to pick up water and become sticky. Precautions were taken to avoid prolonged exposure of the wet filter cake to the atmosphere.

Commercial lactic acid generally contains about 8-12% w/w water, and contains dimers and trimers in addition to the monomeric lactic acid. The mole ratio of lactic acid dimer to monomer is generally about 1.0:4.7. Commercial grade lactic acid may be used in the process described in the preceding paragraph as the monolactate salt preferentially precipitates from the reaction mixture.

It should be understood that the organic compounds according to the invention may exhibit the phenomenon of tautomerism. As the chemical structures within this specification can only represent one of the possible tautomeric forms at a time, it should be understood that the invention encompasses any tautomeric form of the drawn structure. For example, the compound having the formula IIIB is shown below with one tautomer, Tautomer IIIBa:

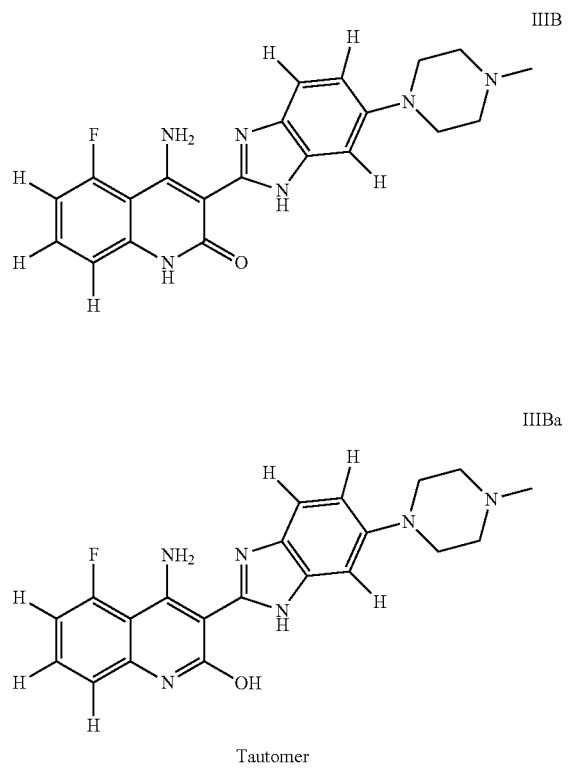

Other tautomers of the compound having the formula IIIB, Tautomer IIIBb and Tautomer IIIBc, are shown below:

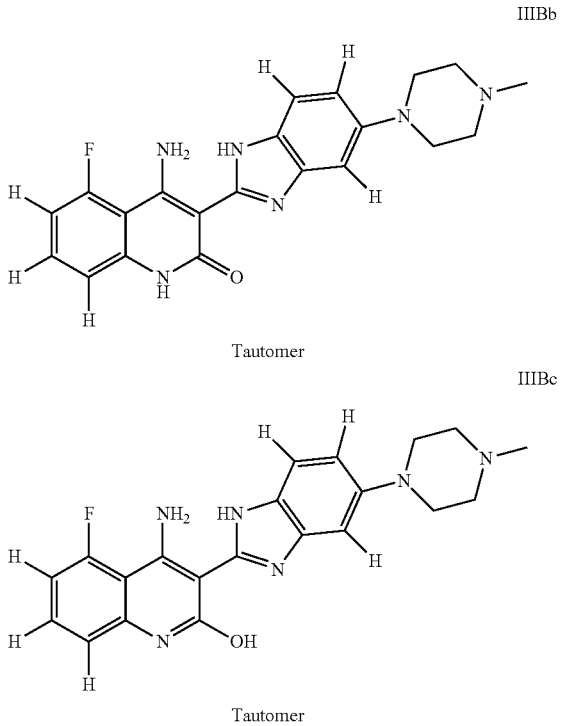

The contents of each of the patents, patent applications and journal articles cited above are hereby incorporated by reference herein and for all purposes as if fully set forth in their entireties.

It is understood that the invention is not limited to the embodiments set forth herein for illustration, but embraces all such forms thereof as come within the scope of the following claims.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:
1. A method for synthesizing a heterocyclic compound, comprising:
reacting a mixture of 1-methylpiperazine and 5-halo-2-nitroaniline in a first solvent and at a first temperature ranging from about 90° C. to about 110° C. to provide a compound of Formula VIH

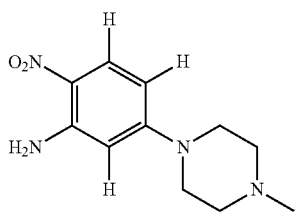

in the first solvent, wherein the first solvent comprises an alcohol;

adding to the mixture a volume of a second solvent, different from the first solvent; wherein the second solvent comprises heptane; and forming a slurry of the compound of Formula VIH.

2. The method of claim 1, wherein the second solvent consists essentially of, or consists of heptane.

3. The method of claim 1 further comprising cooling the mixture containing the compound of Formula VIH to a second temperature not less than 70% of the first temperature before the volume of second solvent is added.

4. The method of claim 3 wherein the second temperature ranges from about 70° C. to about 85° C.

5. The method of claim 4, wherein the slurry is formed by cooling the reaction mixture to a third temperature ranging from about 15° C. to about 25° C. to induce formation of a slurry of the compound of Formula VIH.

6. A method for synthesizing a heterocyclic compound, comprising: in a first reaction mixture, reacting 1-methylpiperazine with 5-halo-2-nitroaniline in a solvent that comprises water and a salt at a temperature greater than 95° C., and cooling the first reaction mixture sufficiently to precipitate a first solid comprising the compound of Formula VIH

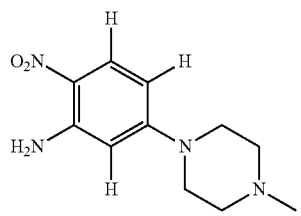

and filtering the first reaction mixture to give a first filtered solid comprising the compound of Formula VIH and a first filtrate comprising the solvent.

7. The method of claim 6, wherein the solvent comprises water in an amount greater than 50 percent by volume based on the amount of the solvent.

8. The method of claim 6, wherein the salt is NaCl.

9. The method of claim 6, wherein the internal temperature ranges from about 99° C. to about 115° C.

10. The method of claim 6, wherein the solvent further comprises an inorganic base.

11. The method of claim 10, wherein the salt is NaCl, and the inorganic base is selected from the group consisting of NaOH, KOH, Ca(OH)$_2$, Mg(OH)$_2$, Na$_2$CO$_3$, K$_2$CO$_3$, and K$_3$PO$_4$.

12. The method of claim 6, further comprising adding to the first filtrate 1-methylpiperazine, 5-halo-2-nitroaniline, and an amount of a base sufficient to neutralize any HCl in the first filtrate, to give a second reaction mixture, at an internal temperature sufficient to provide the compound of Formula VIH.

13. The method of claim 12, further comprising cooling the second reaction mixture sufficiently to precipitate a second solid comprising the compound of Formula VIH and filtering the second reaction mixture to provide a second filtered solid comprising the compound of Formula VIH and a second filtrate comprising the solvent.

14. A method of synthesizing a compound of Formula VIH, comprising reacting 1-methylpiperazine with 5-halo-2-nitroaniline in a solvent that comprises an organic solvent component that has a boiling point of greater than about 100° C. at atmospheric pressure to provide the compound of Formula VIH,

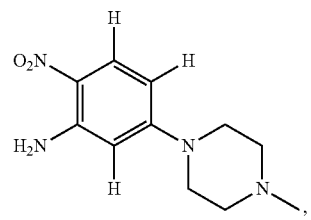

wherein the organic solvent is a compound of Formula HO—(CH$_2$)$_q$—OH or HO—CH$_2$CH$_2$OCH$_2$CH$_2$—OH, wherein q is selected from 2, 3, or 4.

15. The method of claim 14 wherein the solvent comprises ethylene glycol or propylene glycol.

16. The method of claim 14 wherein the 5-halo-2-nitroaniline is 5-chloro-2-nitroaniline or 5-fluoro-2-nitroaniline.

17. A method for synthesizing a heterocyclic compound, comprising: in a first reaction mixture, reacting 1-methylpiperazine with 5-halo-2-nitroaniline in a solvent that comprises water at a temperature greater than 95° C., and cooling the first reaction mixture sufficiently to precipitate a first solid comprising the compound of Formula VIH and a first filtrate comprising the solvent.

18. The method of claim 1, wherein 1-methylpiperazine and 5-halo-2-nitroaniline are present at a molar ratio ranging from about 2:1 to about 5:1.

19. The method of claim 6, wherein the molar ratio of the 1-methylpiperazine to the 5-halo-2-nitroaniline ranges from about 2:1 to about 10:1 at the start of the reaction.

20. The method of claim 10, wherein the concentration of the salt in the aqueous solution ranges from about 1 to about 5 M.

21. The method of claim 20, wherein the concentration of salt in the aqueous solution ranges from about 3 to about 5 M.

22. The method of claim 10, wherein the amount of inorganic base ranges from 0.5 to 4 equivalents based on the amount of 5-halo-2-nitroaniline.

23. The method of claim 10, wherein 1-methylpiperazine and 5-halo-2-nitroaniline are present at a molar ratio ranging from about 1.5:1 to about 3:1.

* * * * *